(12) United States Patent
Gartel et al.

(10) Patent No.: US 8,029,980 B2
(45) Date of Patent: Oct. 4, 2011

(54) IDENTIFICATION AND USE OF AGENTS THAT MODULATE ONCOGENIC TRANSCRIPTION AGENT ACTIVITY

(75) Inventors: Andrei L. Gartel, Chicago, IL (US); Senthil K. Radhakrishnan, Pasadena, CA (US)

(73) Assignee: The Board of Trustees of the University of Illinois, Urbana, IL (US)

(*) Notice: Subject to any disclaimer, the term of this patent is extended or adjusted under 35 U.S.C. 154(b) by 265 days.

(21) Appl. No.: 11/865,410

(22) Filed: Oct. 1, 2007

(65) Prior Publication Data

US 2008/0152618 A1   Jun. 26, 2008

Related U.S. Application Data

(60) Provisional application No. 60/848,476, filed on Sep. 29, 2006, provisional application No. 60/898,613, filed on Jan. 31, 2007.

(51) Int. Cl.
*C12Q 1/00* (2006.01)
*C12Q 1/66* (2006.01)
(52) U.S. Cl. .................................. 435/4; 435/8
(58) Field of Classification Search .................. None
See application file for complete search history.

(56) References Cited

U.S. PATENT DOCUMENTS

| | | | |
|---|---|---|---|
| 4,064,013 A | 12/1977 | Meyers et al. | |
| 5,723,313 A | 3/1998 | Sherr et al. | |
| 6,172,194 B1 | 1/2001 | Sherr et al. | |
| 6,376,175 B1 * | 4/2002 | Foulkes et al. | 435/6 |
| 6,407,062 B1 | 6/2002 | Sherr et al. | |
| 7,635,673 B2 * | 12/2009 | Costa et al. | 514/2 |
| 2002/0155988 A1 | 10/2002 | O'Hare et al. | |
| 2002/0156023 A1 | 10/2002 | Walling et al. | |
| 2002/0193325 A1 | 12/2002 | Depinho | |
| 2005/0032692 A1 | 2/2005 | Costa et al. | |
| 2006/0014688 A1 | 1/2006 | Costa et al. | |
| 2009/0075376 A1 | 3/2009 | Cossta et al. | |

FOREIGN PATENT DOCUMENTS

| | | |
|---|---|---|
| WO | WO0160374 A1 | 8/2001 |
| WO | WO0226236 A1 | 4/2002 |
| WO | WO02083140 A1 | 10/2002 |
| WO | WO02092013 A3 | 11/2002 |
| WO | WO2004018676 A2 | 3/2004 |
| WO | WO2004019761 A2 | 3/2004 |
| WO | WO2004100977 A1 | 11/2004 |
| WO | WO2005054870 A2 | 6/2005 |
| WO | WO2006/009575 A1 | 1/2006 |
| WO | WO2007109609 A2 | 9/2007 |
| WO | WO2008095112 A3 | 8/2008 |

OTHER PUBLICATIONS

Bowie (Science, 1990, 257:1306-1310).*
By Burgess et al ( J of Cell Bio. 111:2129-2138, 1990).*
Lazar et al (Molecular and Cellular Biology, 1988, 8:1247-1252).*
Harris et al. J. of The Am Society of Nephrology 6:1125-33, 1995.*
Ahn et al. Nature Genetics 3(4):283-91, 1993.*
Cawthon et al. Genomics 9(3):446-60, 1991).*
Laoukili et al., "FoxM1 is Required for Execution of the Mitotic Programme and Chromosome Stability", Nature Cell Biology, vol. 7, No. 2, Feb. 2005, pp. 126-136; pp. 1-4.
Wang et al., "Forkhead Box M1 Regulates the Transcriptional Network of Genes Essential for Mitotic Progression and Genes Encoding the SCF (Skp2-Cks1) Ubiquitin Ligase", Molecular and Cellular Biology, Dec. 2005, vol. 25, No. 24, pp. 10875-10894.
Robert H. Costa, "FoxM1 Dances With Mitosis", Nature Cell Biology, vol. 7, No. 2, Feb. 2005, pp. 108-110.
Ye et al., "Hepatocyte Nuclear Factor 3/Fork Head Homolog 121 is Expressed in Proliferating Epithelial and Mesenchymal Cells of Embryonic and Adult Tissues", Molecular and Cellular Biology, vol. 17, No. 3, Mar. 1997, pp. 1626-1641.
Ye et al., "Premature Expression of the Winged Helix Transcription Factor HFH-11B in Regenerating Mouse Liver Accelarates Hepatocyte Entry into S Phase", Molecular and Cellular Biology, Vo. 19, No. 12, Dec. 1999, pp. 8570-8580.
Korver et al., "The Winged-helix Transcription Factor Trident is Expressed in Cycling Cells", Nucleic Acids Research, 1997, vol. 25, No. 9, pp. 1715-1719.
Yao et al., "Molecular Analysis of a Novel Winged Helix Protein, WIN", The Journal of Biological Chemistry, vol. 272, No. 32, Issue of Aug. 8, 1997, pp. 19827-19836.
Wonsey et al., "Loss of the Forkhead Transcription Factor FoxM1 Causes Centrosome Amplification and mitotic Catastrophe", Cancer Research 2005; 65: (12) Jun. 15, 2005, pp. 5181-5189. Teh et al., "FoxM1 is a Downstream Target of Gli1 in Basal Cell Carcinomas", Cancer Research 62, Aug. 15, 2002, pp. 4773-4780.
Okabe et al., "Genome-wide Analysis of Gene Expression in Human Hepatocellular Carcinomas Using cDNA Microarray: Identification of Genes Involved in viral Carcinogenesis and Tumor Progression", Cancer Research 61, Mar. 1, 2001, pp. 2129-2137.
Lee et al., "Classification and Prediction of Survival in Hepatocellular Carcinoma by Gene Expression Profiling", Hepatology, Vo. 40, No. 3, Sep. 2004, pp. 667-676.
Obama et al., "Genome-Wide Analysis of Gene Expression in Human Intrahepatic Cholangiocarcinoma", Hepatology, vol. 41, No. 6, Jun. 2005, pp. 1339-1348.
Kim et al., "The Forkhead Box m1 Transcription Factor Stimulates the Proliferation of Tumor Cells during Development of Lung Cancer", Cancer Research, 66: (4), Feb. 15, 2006, pp. 2153-2161.

(Continued)

*Primary Examiner* — Laura B Goddard
(74) *Attorney, Agent, or Firm* — McDonnell Boehnen Hulbert & Berghoff LLP

(57) ABSTRACT

Embodiments of the invention provides, among other things, methods for identifying agents that inhibit oncogenic transcription factors, induce apoptosis, inhibit the growth of transformed cells and cancer cells, and potentiate the effects of other agents that induce apoptosis and that inhibit the growth of transformed cells and cancer cells. Embodiments of the invention further provide compositions useful for the same comprising an agent the inhibits one or more oncogenic transcription factors and an agent that induces apoptosis, particular compositions wherein the apoptotic effect of the combination is greater than either agent by itself. Embodiments of the invention further provide for the use of such agents and compositions to treat cancer. In illustrative embodiments the agents that inhibit transcription factor activity are thiazole antibiotics, such as Siomycin and thiostrepton, and the apoptosis inducing agent is a member of the TNF ligand superfamily, such as TNF-alpha. In illustrative embodiments the cancers are those in which both the FoxM1 and the NF-kB oncogenic pathways are activated.

11 Claims, 16 Drawing Sheets

OTHER PUBLICATIONS van den Boom et al., "Characterization of Gene Expression Profiles Associated with Glioma Progression Using Oligonucleotide-Based Microarray Analysis and Real-Time Reverse Transcription-Polymerase Chain Reaction", American Journal of Pathology, vol. 163, No. 3, Sep. 2003, pp. 1033-1043.

Kalin et al., "Increased Levels of the FoxM1 Transcription Factor Accelerate Development and Progression of Prostate Carcinomas in both TRAMP and LADY Transgenic Mice". Cancer Research, Feb. 1, 2006; 66(3): pp. 1712-1720.

Pilarsky et al., "Identification and Validation of Commonly Overexpressed Genes in Solid Tumors by Comparison of Microarray Data". Neoplasia, vol. 6, No. 6, Nov./Dec. 2004, pp. 744-750.

Kalinichenko et al., "Foxm1b Transcription Factor is Essential for Development of Hepatocellular Carcinomas and is Negatively Regulated by the p19 ARF Tumor Suppressor". Genes & Development, 2004, 18: pp. 830-850.

Radhakrishnan et al., "Constitutive Expression of E2F-1 Leads to P21-Dependent Cell Cycle Arrest in S Phase of the Cell Cycle", Oncogene, 2004, 23, pp. 4173-4176.

Radhakrishnan et al., "The PPAR-Y Agonist Pioglitazone Post-Transcriptionally Induces p21 in PC3 Prostate Cancer but not in Other Cells Lines", Cell Cycle, vol. 4, Issue 4, 2005, pp. 582-584.

Radhakrishnan et al., "Multiple Alternate p21 Transcripts are Regulated by p53 in Human Cells". Oncogene (2006) 25, pp. 1812-1815.

Cozen et al., "Induction of Cell Cycle Progression and Acceleration of Apoptosis are two Separable Functions of c-Myc: Transrepression Correlates with Acceleration of Apoptosis". Molecular and Cellular Biology, vol. 20, No. 16, Aug. 2000, pp. 6008-6018.

Major et al., "Forkhead Box M1B Transcription Activity Requires Binding of Cdk-Cyclin Complexes for Phosphorylation-Dependent Recruitment of p300/CBP Coactivators". Molecular and Cellular Biology, vol. 24, No. 7, Apr. 2004, pp. 2649-2661.

Lentzen et al. "Structural Basis for Contrasting Activities of Ribosome Binding Thiazole Antibiotics". Chemistry & Biology, vol. 10, Aug. 2003, pp. 769-778.

Radhakrishnan et al., "A Novel Transcriptional Inhibitor Induces Apoptosis in Tumor Cells and Exhibits Antiangiogenic Activity". Cancer Research, vol. 66, No. 6, Mar. 15, 2006, pp. 3264-3270.

Weinstein, "Addiction to Oncogenes—the Achilles Heal of Cancer". Science, vol. 297, Jul. 5, 2002, pp. 63-64.

Hagg et al. "A Novel High-through-Put Assay for Screening of Pro-Apoptotic Drugs". Investigational New Drugs, vol. 20, 2002, pp. 253-259.

Erdal et al., "Induction of Lysosomal Membrane Permeabilization by Compounds That Activate p53 Independent Apoptosis". PNAS, Jan. 4, 2005, vol. 102, No. 1, pp. 192-197.

Monga et al., "Developmental Therapeutics Program at the NCI: Molecular Target and Drug Discovery Process". Leukemia (2002) 16, pp. 520-526.

Nicolaou et al., "Discovery of a Biologically Active Thiostrepton Fragment". J. Am. Chem. Soc., 2005, 127 (43), pp. 15042-15044.

Radhakrishnan et al., "Identification of a Chemical Inhibitor of the Oncogenic Transcription Factor Forkhead Box M1". Cancer Research, vol. 66. No. 19, Oct. 1, 2006, pp. 9731-9735.

Madureira et al., "The Forkhead Box M1 Protein Regulates the Transcription of the Estrogen Receptor Alpha in Breast Cancer Cells". Journal of Biological Chemistry, vol. 281, No. 35, Sep. 1, 2006, pp. 25167-25176.

Smith et al., "The TNF Receptor Superfamily of Cellular and Viral Proteins: Activation, Costimulation, and Death". Cell, vol. 76, Mar. 25, 1994, pp. 959-962.

Ashkenazi et al., "Apoptosis Control by Death and Decoy Receptors". Cell Biology, vol. 11, 1999, pp. 255-260.

Ashkenazi et al., "Death Receptors: Signaling and Modulation". Science, vol. 281, No. 5381, Aug. 28, 1998, pp. 1305-1308.

Schulze-Osthoff et al., "Apoptosis Signaling by Death Receptors". Eur. J. Biochem., vol. 254, 1998, pp. 439-459.

van Antwerp et al., "inhibition of TNF-Induced Apoptosis by NF-kB". Trends in Cell Biology, vol. 8, Mar. 1998, pp. 107-111.

Nagata and Golstein., "The fas death factor". Science 267, No. 5203, Mar. 10, 1995, pp. 1449-1456.

Griffith et al., "TRAIL: A Molecule with Multiple Receptors and Control Mechanisms". Current Opinion in Immunology 1998, 10:559-563.

Yeh et al., "FADD: Essential for Embryo Development and Signaling from some, but not all inducters of apoptosis". Science 279, No. 5358, Mar. 20, 1998, pp. 1954-1957.

Muzio et al., "FLICE, A Novel FADD-Homologous ICE/CED-3-Like Protease, is Recruited to the CD95 (Fax/APO-1) Death-Inducing Signaling Complex". Cell, vol. 85, Jun. 14, 1996, pp. 817-827.

Hsu et al., "TRADD-TRAF2 and TRADD-FADD Interactions Define Two Distinct TNF Receptor 1 Signal Transduction Pathways". Cell, vol. 84, Jan. 26, 1996, pp. 299-308.

Boldin et al., Involvement of MACH, a Novel MORT1/FADD-Interactiing Protease, in Fax/APO-1-and TNF Receptor-Induced Cell Death. Cell, vol. 85, Jun. 14, 1996, pp. 803-815.

Asakawa, K., et al., "Human Growth Hormone Stimulates Liver Regeneration in Rats," J. Endocrinol. Invest, 1989, vol. 12, pp. 343-347.

Barle, Hans, et al., "Depression of Liver Protein Synthesis During Surgery is Prevented by Growth Hormone," American Physiological Society, 1999, 276 (4 Pt 1) pp. E620-627.

Chandran, Uma, R., et al., "Gene Expression of Profiles of Prostate Cancer Reveal Involvement of Multiple Molecular Pathways in the Metastatic Process," BMC Cancer, 2007, 7:64, from the World Wide Web <http://www.biomedcentral.com/1471-2407/7/64>.

Charrier, Martal J., et al., Retraction "Growth Horomones. 1. Polymorphism (minireview)," Reprod. Nutr. Dev., 1988, 28 (4A), pp. 857-887.

Curti, Crit. Rev. in Oncology/hematology, 1993, 14:29-39.

Dermer, Bio/Technology, 1994, 12:320.

Douard, Richard, et al., "Sonic Hedgehog-Dependent Proliferation in a Series of Patents with Colorectal Cancer," Surgery 2006, pp. 665-670.

Freshney, Culture of Animal Cells, A Manual of Basic Technique, Alan R. Liss, Inc., 1983, New York, p4.

Gura (Science, 1997), 278:1041-1042.

Gusarova, Galina, A., et al., "A Cell-Penetrating ARF Peptide Inhibitor of FoxM1 in mouse Hepatocellular Carcinoma Treatment," The Journal of Clinical Investigation, 2007, vol. 117, No. 1, pp. 99-111.

Jain, Sci. Am., 1994, 271:58-65.

Johnson and Tracey, 'Peptide and Protein Drug Delivery', In: Encyclopedia of Controlled Drug Delivery, vol. 2, 1999, pp. 816-833.

Katoh, Masuko, "Human FOX Gene Family (Review)," International Journal of Oncology, 2004, vol. 25, No. 5, pp. 1495-1500.

Korver, et al., "The Human TRIDENT/HFG-11/FKHL 16 Gene: Structure, Localization, and Promoter Characterization" Genomics 46:435-442 (1997).

Krupczak-Hollis et al., "Growth Hormone Stimulates Proliferation of Old-Aged Regenerating Liver Through Forkhead Box m1b" Hepatology 38(6) 1552-62 (Dec. 2003).

Laes, et al., Cancer Genet Cytogenet 117:118-124, 2000.

Luscher-Firzlaff, Juliane M., et al., "Interaction of the Fork Head Domain Transcription Factor MPP2 with the Human Papilloma Virus 16 E7 Protein: Enhancement of Transformation and Transactivation," Oncogene, 1999, vol. 18, pp. 5620-5630.

Ly, Danith H., et al., "Mitotic Misregulation and Human Aging," Science, 2000, vol. 287, pp. 2486-2492.

Potente, Michael, et al., "11, 12-Epoxyeicosatrienoic Acid-Induced Inhibition FOXO Factors Promotes Endothelial Proliferation by Down-Regulating p27Kip1," The Journal of Biological Chemistry, 2003, vol. 278, No. 32, pp. 29619-29625.

Supriatno et al., "Overexpression of p27kip1 induces growth arrest and apoptosis in an oral cancer cell line" Oral Oncology 38(7)730-736 (2002).

Wang, X., et al., "Increased Levels of Forkhead box M1B Transcription Factor in Transgenic Mouse Hepatocytes Prevent Age-Related Proliferation Defects in Regenerating Liver," PNAS, Sep. 25, 2001, vol. 98, No. 20, pp. 11468-11473.

Wang, et al., "Increased Hepatic Forkhead Box M1B (FoxM1B) Levels in Old-aged Mice Stimulated Liver Regarneration through Diminished p27Kip1", Journal of Biological Chemistry 277(46) 44310-16 (Nov. 15, 2002).

Wang, Xinhe et al., "The Forkhead Box m1b transcription factor is essential for hepatocite DNA replication and mitosis during mouse liver regeneration" PNAS 99(26) 16881-6 (Dec. 24, 2002).

Wang, et al., "Earlier Expression of the Transcription Factor HFH-11B Diminishes Induction of p21CIPI/WAF1 Levels and Accelerates Mouse Hepatocyte Entry Into S-Phase Following Carbon Tetrachloride Liver Injury," Hepatology, 2001, vol. 33, No. 6, pp. 1-11.

Wang, I-C, et al., "Transgenic Expression of the Forkhead Box M1 Transcription Factor Induces Formation of Lung Tumors," Oncogene, 2008, pp. 1-13.

Zips, In Vivo, 2005, 19:1-8.

* cited by examiner

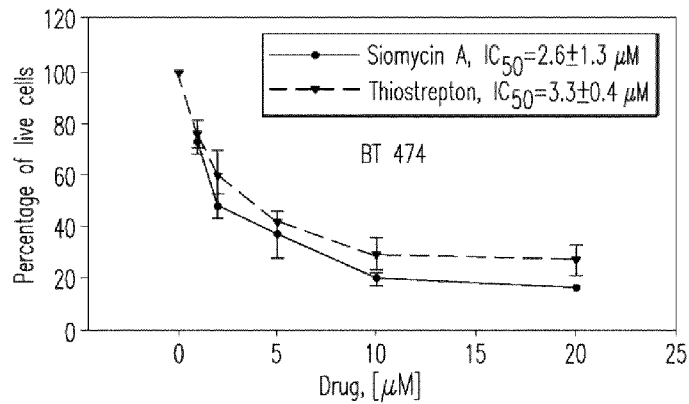
FIG. 12A1
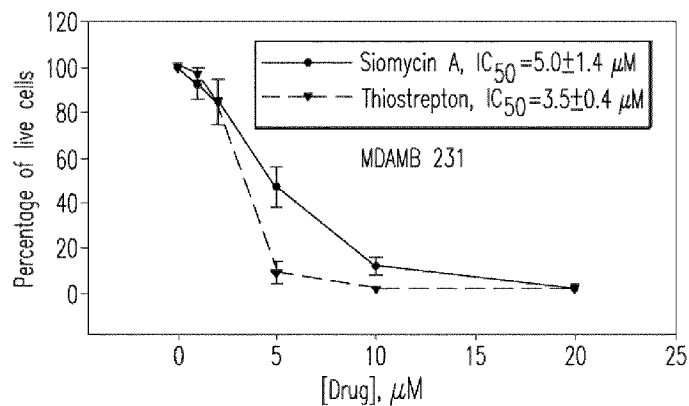
FIG. 12A2
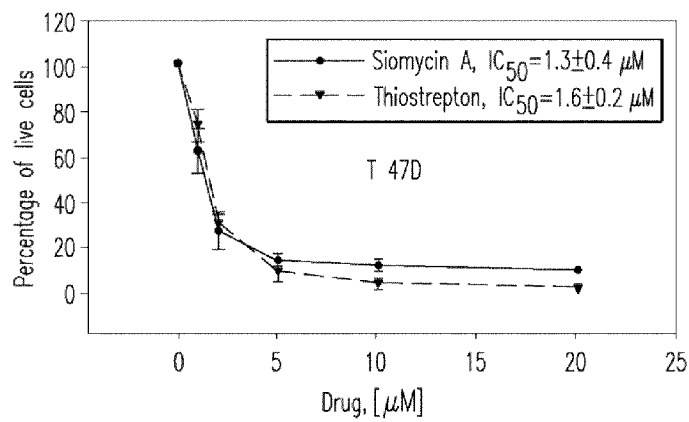
FIG. 12A3

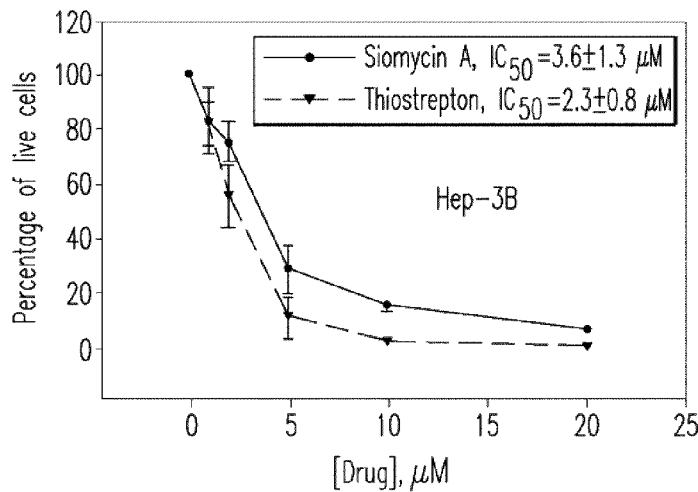
FIG.12B1
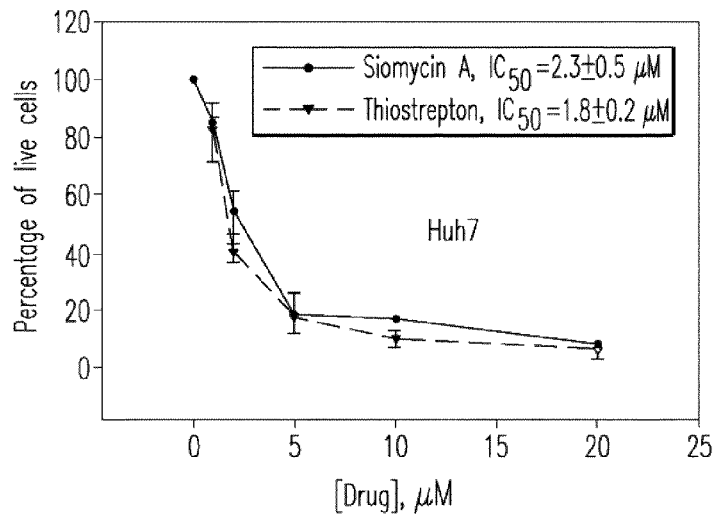
FIG.12B2
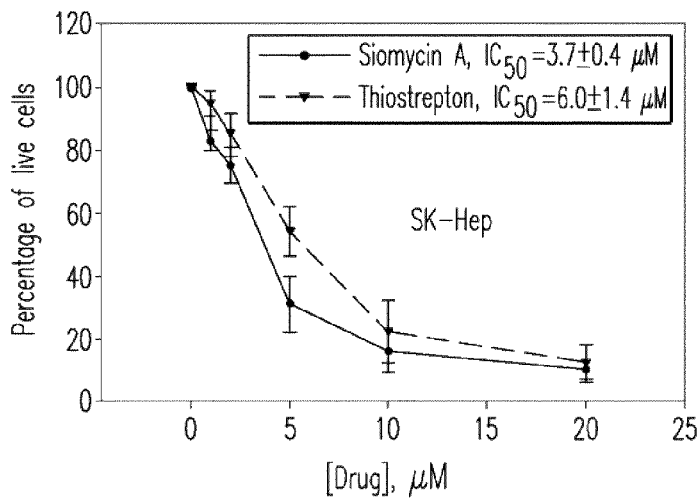
FIG.12B3

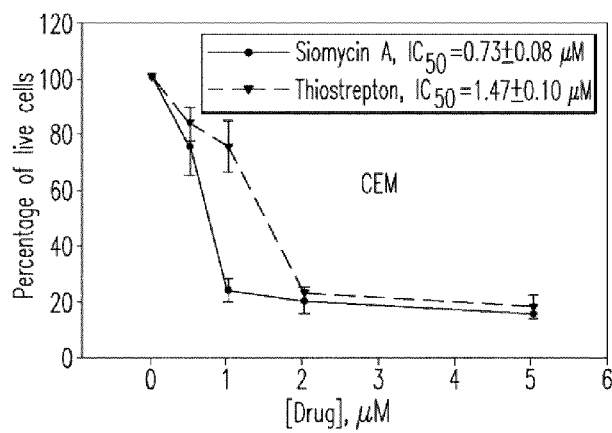
FIG.12C1
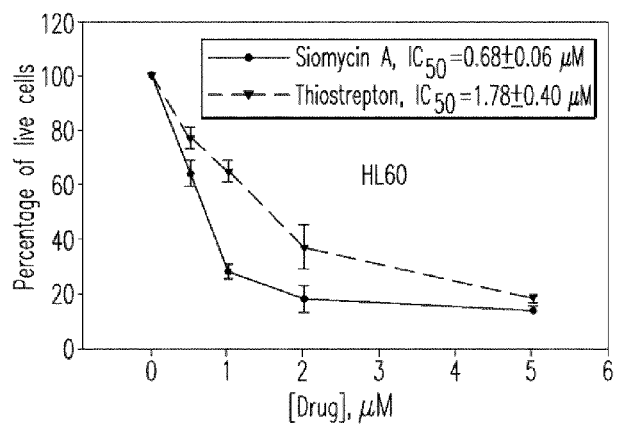
FIG.12C2
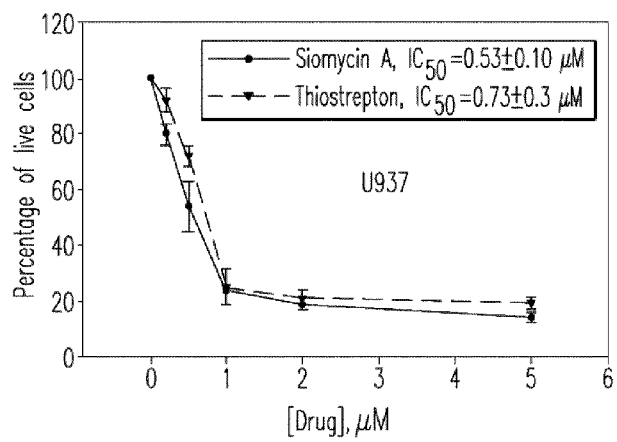
FIG.12C3

SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
ggaggaaatg ccacacttag cg                                          22

<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
taggacttct tgggtcttgg ggtg                                              24

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
tcaaggacca ccgcatctct a                                                 21

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
tgaagcagaa gaaacactgg gc                                                22

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
attcagacag tgaggaagag gacg                                              24

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
catcaatggg gaaggaggtc ag                                                22

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
cccttccctg ttttcctttc                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
acacacactc ctgccatagg                                                   20

<210> SEQ ID NO 9
<211> LENGTH: 22
<212> TYPE: DNA
<213> ORGANISM: Artificial Sequence

```
<220> FEATURE:
<223> OTHER INFORMATION: Synthetic primer

<400> SEQUENCE: 9
gcagacaagg tcccaaagac ag                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
caccctgaca cataaaccct gg                                              22

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tgcccagcag tctcttacct                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
accttctggc agtctctgga                                                 20

<210> SEQ ID NO 13
<211> LENGTH: 2247
<212> TYPE: DNA
<213> ORGANISM: Homo sapiens

<400> SEQUENCE: 13
atgaaaacta gccccgtcg gccactgatt ctcaaaagac ggaggctgcc ccttcctgtt      60
caaaatgccc caagtgaaac atcagaggag gaacctaaga gatcccctgc ccaacaggag    120
tctaatcaag cagaggcctc caaggaagtg gcagagtcca actcttgcaa gtttccagct    180
gggatcaaga ttattaacca ccccaccatg cccaacacgc aagtagtggc catccccaac    240
aatgctaata ttcacagcat catcacagca ctgactgcca agggaaaaga gagtggcagt    300
agtgggccca acaaattcat cctcatcagc tgtgggggag ccccaactca gcctccagga    360
ctccggcctc aaacccaaac cagctatgat gccaaaagga cagaagtgac cctgagacc    420 ttgggaccaa aacctgcagc tagggatgtg aatcttccta gaccacctgg agcccttgc    480 gagcagaaac gggagacctg tgcagatggt gaggcagcag gctgcactat caacaatagc    540
ctatccaaca tccagtggct tcgaaagatg agttctgatg gactgggctc ccgcagcatc    600
aagcaagaga tggaggaaaa ggagaattgt cacctggagc agcgacaggt taaggttgag    660
gagccttcga gaccatcagc gtcctggcag aactctgtgt ctgagcggcc acctactct    720 tacatggcca tgatacaatt cgccatcaac agcactgaga ggaagcgcat gactttgaaa    780
gacatctata cgtggattga ggaccacttt ccctactta agcacattgc caagccaggc    840
tggaagaact ccatccgcca caccctttcc ctgcacgaca tgtttgtccg ggagacgtct    900
```

```
gccaatggca aggtctcctt ctggaccatt caccccagtg ccaaccgcta cttgacattg    960
gaccaggtgt ttaagcagca gaaacgaccg aatccagagc tccgccggaa catgaccatc   1020
aaaaccgaac tcccccctggg cgcacggcgg aagatgaagc cactgctacc acgggtcagc   1080
tcatacctgg tacctatcca gttcccggtg aaccagtcac tggtgttgca gccctcggtg   1140
aaggtgccat tgcccctggc ggcttccctc atgagctcag agcttgcccg ccatagcaag   1200
cgagtccgca ttgcccccaa ggtgctgcta gctgaggagg ggatagctcc tctttcttct   1260
gcaggaccag ggaaagagga gaaactcctg tttggagaag ggttttctcc tttgcttcca   1320
gttcagacta tcaaggagga agaaatccag cctggggagg aaatgccaca cttagcgaga   1380
cccatcaaag tggagagccc tcccttggaa gagtggccct ccccggcccc atctttcaaa   1440
gaggaatcat ctcactcctg gaggattcg tcccaatctc ccaccccaag acccaagaag    1500
tcctacagtg ggcttaggtc cccaacccgg tgtgtctcgg aaatgcttgt gattcaacac   1560
agggagagga gggagaggag ccggtctcgg aggaaacagc atctactgcc tccctgtgtg   1620
gatgagccgg agctgctctt ctcagagggg cccagtactt cccgctgggc cgcagagctc   1680
ccgttcccag cagactcctc tgaccctgcc tcccagctca gctactccca ggaagtggga   1740
ggaccttta agacacccat taaggaaacg ctgcccatct cctccacccc gagcaaatct    1800
gtcctcccca gaaccctga atcctggagg ctcacgcccc cagccaaagt aggggggactg   1860
gatttcagcc cagtacaaac ctcccagggt gcctctgacc ccttgcctga cccctgggg    1920
ctgatggatc tcagcaccac tcccttgcaa agtgctcccc cccttgaatc accgcaaagg   1980
ctcctcagtt cagaacccct tagacctcatc tccgtcccct ttggcaactc ttctcccctca   2040
gatatagacg tccccaagcc aggctccccg gagccacagg tttctggcct tgcagccaat   2100
cgttctctga cagaaggcct ggtcctggac acaatgaatg acagcctcag caagatcctg   2160
ctggacatca gctttcctgg cctggacgag gacccactgg gccctgacaa catcaactgg   2220
tcccagttta ttcctgagct acagtag                                        2247
```

<210> SEQ ID NO 14
<211> LENGTH: 748
<212> TYPE: PRT
<213> ORGANISM: Homo sapiens

<400> SEQUENCE: 14

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
                20                  25                  30

Lys Arg Ser Pro Ala Gln Gln Glu Ser Asn Gln Ala Glu Ala Ser Lys
            35                  40                  45

Glu Val Ala Glu Ser Asn Ser Cys Lys Phe Pro Ala Gly Ile Lys Ile
        50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
```

-continued

```
            130                 135                 140
Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
                180                 185                 190

Asp Gly Leu Gly Ser Arg Ser Ile Lys Gln Glu Met Glu Glu Lys Glu
            195                 200                 205

Asn Cys His Leu Glu Gln Arg Gln Val Lys Val Glu Glu Pro Ser Arg
210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
                260                 265                 270

Phe Lys His Ile Ala Lys Pro Gly Trp Lys Asn Ser Ile Arg His Asn
            275                 280                 285

Leu Ser Leu His Asp Met Phe Val Arg Glu Thr Ser Ala Asn Gly Lys
290                 295                 300

Val Ser Phe Trp Thr Ile His Pro Ser Ala Asn Arg Tyr Leu Thr Leu
305                 310                 315                 320

Asp Gln Val Phe Lys Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
                340                 345                 350

Lys Pro Leu Leu Pro Arg Val Ser Ser Tyr Leu Val Pro Ile Gln Phe
            355                 360                 365

Pro Val Asn Gln Ser Leu Val Leu Gln Pro Ser Val Lys Val Pro Leu
370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Glu Lys Leu Leu Phe Gly
            420                 425                 430

Glu Gly Phe Ser Pro Leu Leu Pro Val Gln Thr Ile Lys Glu Glu Glu
            435                 440                 445

Ile Gln Pro Gly Glu Glu Met Pro His Leu Ala Arg Pro Ile Lys Val
450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
                500                 505                 510

Ser Glu Met Leu Val Ile Gln His Arg Glu Arg Arg Glu Arg Ser Arg
                515                 520                 525

Ser Arg Arg Lys Gln His Leu Leu Pro Pro Cys Val Asp Glu Pro Glu
            530                 535                 540

Leu Leu Phe Ser Glu Gly Pro Ser Thr Ser Arg Trp Ala Ala Glu Leu
545                 550                 555                 560
```

-continued

```
Pro Phe Pro Ala Asp Ser Ser Asp Pro Ala Ser Gln Leu Ser Tyr Ser
            565                 570                 575
Gln Glu Val Gly Gly Pro Phe Lys Thr Pro Ile Lys Glu Thr Leu Pro
            580                 585                 590
Ile Ser Ser Thr Pro Ser Lys Ser Val Leu Pro Arg Thr Pro Glu Ser
        595                 600                 605
Trp Arg Leu Thr Pro Pro Ala Lys Val Gly Gly Leu Asp Phe Ser Pro
        610                 615                 620
Val Gln Thr Ser Gln Gly Ala Ser Asp Pro Leu Pro Asp Pro Leu Gly
625                 630                 635                 640
Leu Met Asp Leu Ser Thr Thr Pro Leu Gln Ser Ala Pro Pro Leu Glu
            645                 650                 655
Ser Pro Gln Arg Leu Leu Ser Ser Glu Pro Leu Asp Leu Ile Ser Val
            660                 665                 670
Pro Phe Gly Asn Ser Ser Pro Ser Asp Ile Asp Val Pro Lys Pro Gly
            675                 680                 685
Ser Pro Glu Pro Gln Val Ser Gly Leu Ala Ala Asn Arg Ser Leu Thr
        690                 695                 700
Glu Gly Leu Val Leu Asp Thr Met Asn Asp Ser Leu Ser Lys Ile Leu
705                 710                 715                 720
Leu Asp Ile Ser Phe Pro Gly Leu Asp Glu Asp Pro Leu Gly Pro Asp
            725                 730                 735
Asn Ile Asn Trp Ser Gln Phe Ile Pro Glu Leu Gln
            740                 745
```

IDENTIFICATION AND USE OF AGENTS THAT MODULATE ONCOGENIC TRANSCRIPTION AGENT ACTIVITY

REFERENCE TO RELATED APPLICATIONS

This application is a continuation-in-part of and claims full benefit of priority of U.S. provisional application No. 60/848,476, filed on 29 Sep. 2006, and of U.S. provisional application No. 60/898,613, filed on 31 Jan. 2007, each of which is herein incorporated by reference in its entirety.

STATEMENT REGARDING GOVERNMENT FUNDING

This invention was made with government support under grant DK54887-07, awarded by USPHS, and grant BC052816, awarded by the Department of Defense. The government has certain rights in the invention.

FIELD OF THE INVENTION

Embodiments of the invention relate to the field of oncogenic transcription factors, to agents that modulate their activity, to methods for identifying such factors, and to the use of the agents, alone and in combination with other factors, to inhibit the growth of transformed cells, to induce apoptosis, and to treat cancers.

BACKGROUND

Oncogenic transcription factors are important mediators of process involved in cell growth, differentiation, and de-differentiation, and they play important roles in oncogenesis, cancer progression, and metastasis.

For instance, the forkhead box (Fox) family of transcription factors plays important roles in regulating cellular proliferation, differentiation, longevity, and cellular transformation. Wang et al., Proc. Natl. Acad. Sci. USA 98:11468-11473 (2001). The mammalian transcription factor Forkhead Box M1 (FoxM1; previously known as HFH-11B, Trident, WIN, or MPP2) is induced during the G1 phase of the cell cycle, and its expression continues through the S phase and mitosis (1). FoxM1 is especially important for the execution of the mitotic program as seen by the failure of FoxM1-depleted cells to progress beyond the prophase stage of mitosis (2). This is consistent with the demonstration that FoxM1 transcriptionally upregulates a number of target genes including Cyclin B, Survivin, Aurora B kinase, Cdc25b phosphatase, and Plk1, all of which are implicated in mitosis (2, 3). Also, FoxM1 transcriptionally induces Skp2 and Cks1 (specificity subunits of Skp1-Cullin1-F-box ubiquitin ligase complex) leading to the degradation of cyclin-dependent kinase inhibitors $p21^{WAF1}$ and $p27^{KIP1}$, thereby resulting in cell cycle progression (2). In line with its pro-proliferative nature, while FoxM1 is expressed in all dividing mammalian cells and tumor-derived cells, its expression is turned off in terminally differentiated cells (4-7).

FoxM1 is overexpressed significantly in primary breast tumors (8), basal cell carcinomas (9), hepatocellular carcinomas (10, 11), intrahepatic cholangiocarcinomas (12), non-small cell lung cancers (13), anaplastic astrocytomas, and glioblastomas (14). Also, increased levels of FoxM1 has been seen to accelerate prostate cancer development and progression in mouse models (15). Furthermore, a large-scale analysis of microarray results revealed that FoxM1 is one of the most common genes overexpressed in a majority of solid tumors (16). Together, these studies indicate that FoxM1 could be an attractive target for anti-cancer therapy. This notion is supported by a recent finding that depletion of FoxM1 by RNA interference (RNAi) in breast cancer cells leads to mitotic catastrophe (8). In a similar manner, knockdown of FoxM1 by small interfering RNAs (siRNAs) in several prostate and lung cancer cell lines was shown to lead to a significant reduction in cell proliferation and anchorage-independent cell growth on soft agar (13, 15). Consistent with these observations, inhibition of FoxM1 transcriptional activity by a peptide containing amino acids 24-46 of $p19^{ARF}$ also reduced anchorage independent cell growth (17).

The central role of oncogenic transcription factors, such as FoxM1, in regulating cell growth, proliferation, and differentiation, and in pathologies associated with changes in their functioning, such as cancers, makes them attractive targets for drug development. Accordingly, there has been a great deal of research and development work not only on characterizing these factors and their roles in cellular and disease processes, but also on therapeutic agents that modulate their activity. Although these efforts have resulted in some success, the agents that have been developed thus far are far from ideal. There is a need therefore for improved methods of identifying agents that modulate the activity of oncogenic transcription factors, and for the agents themselves, as well as for formulations comprising the agents and for methods of using the agents and composition to treat diseases, such as malignancies and cancers.

SUMMARY OF THE INVENTION

It is therefore among the many objects of the invention to provide methods for screening (identifying) agents that modulate the activity of oncogenic transcriptions factors, particularly inhibitors, to provide the agents themselves, to provide formulations of the agents, particularly pharmaceutically acceptable formulations, and to provide treatments for diseases, such as malignancies and cancers, that utilize the agents and formulations. Many other objects of the invention will be clearly ascertained as well by a thorough reading of the entirety of the present disclosure.

Screening Methods of the Invention

In various embodiments, the invention provides methods for screening for an agent that modulates the activity of an oncogenic transcription factor. One such oncogenic transcription factor is FoxM1. In various embodiments the methods comprise exposing a sample to an agent to be tested, detecting a level of activity of the oncogenic transcription factor, and comparing the level of activity of the oncogenic transcription factor to a control level. In various embodiments the oncogenic transcription factor activity detected and compared is the promoter activity wherein a reporter construct containing a promoter responsive to the oncogenic transcription factor is used. In various embodiments a second reporter controlled by a constitutive promoter is used as a control for compounds toxic to the sample and for general transcriptional and/or translational inhibitors. In various embodiments the methods are used in a high throughput fashion for screening inhibitors that repress expression of the first reporter, but not the second reporter. Samples that are screened may be, among other things, tissue samples or cell culture samples.

In accordance with the foregoing, oncogenic transcription factors, such as FoxM1, and cells that produce them, may be made by methods known to the skilled artisan. For example, a nucleotide sequence encoding the FoxM1 gene may be introduced into a desired host cell. Such a nucleotide sequence may first be inserted into an appropriate recombinant expression vector.

The FoxM1 may be encoded by a nucleotide sequence that has at least about 60%, at least about 70%, at least about 80%, or at least about 90% identity to the FoxM1 nucleotide sequence set forth in Genbank accession number U74613 (polynucleotide and polypeptide sequences are shown in SEQ ID NO:13 and SEQ ID NO:14, respectively), which is incorporated by reference. The same applies to homology with the sequences of other oncogenic transcription factors.

Recombinant expression vectors may be constructed by incorporating nucleotide sequences within a vector according to methods well known to the skilled artisan. A wide variety of vectors are known that are useful in the invention in this regard. Suitable vectors include plasmid vectors and viral vectors, including retrovirus vectors, adenovirus vectors, adeno-associated virus vectors and herpes viral vectors. The vectors may include other known genetic elements necessary or desirable for efficient expression of the nucleic acid in a specified host cell, including regulatory elements. For example, the vectors may include a promoter and any necessary enhancer sequences that cooperate with the promoter to achieve transcription of the gene. The nucleotide sequence may be operably linked to such regulatory elements.

Such a nucleotide sequence is referred to as a "genetic construct." A genetic construct may contain a genetic element on its own or in combination with one or more additional genetic elements, including but not limited to genes, promoters, or enhancers. In some embodiments, these genetic elements are operably linked. In some embodiments, the specific gene at issue (for example, FoxM1) may not be present in the genetic construct, including, but not limited to, a situation in which a FoxM1 responsive promoter is operably linked to a reporter gene.

As used herein, a nucleotide sequence is "operably linked" to another nucleotide sequence when it is placed in a functional relationship with another nucleotide sequence. For example, if a coding sequence is operably linked to a promoter sequence, this generally means that the promoter may modulate (e.g., promote) transcription of the coding sequence, or if a ribosome binding site is operably linked to a coding sequence, this generally means that it is positioned so as to facilitate translation. "Operably linked" means that the DNA sequences being linked are typically contiguous and, where necessary to join two protein coding regions, contiguous and in reading frame. However, since enhancers may function when separated from the promoter by several kilobases and intron sequences may be of variable lengths, some nucleotide sequences may be operably linked but not contiguous or not in reading frame. In some embodiments, linking can be accomplished by ligation at convenient binding sites, or if such sites do not exist, synthetic oligonucleotide adaptors or linkers can be used in accord with conventional practice.

A wide variety of methods are available for introducing the nucleotide sequence encoding FoxM1 or FoxM1 fragments, which may be included in a recombinant expression vector, into a host cell. Such methods are known to the art and include mechanical methods, chemical methods, lipophilic methods, and electroporation. Microinjection and use of a gene gun with, for example, a gold particle substrate for the DNA to be introduced, is a representative, non-limiting exemplary mechanical method. Use of calcium phosphate or DEAE-Dextran is a representative, non-limiting exemplary chemical method. Exemplary lipophilic methods include use of liposomes and other cationic agents for lipid-mediated transfection. Such methods are well known to the art, such as, for instance, human cells.

A wide variety of host cells may be utilized in the present invention to produce FoxM1 and screen for agents that modulate FoxM1. Such cells include, but are not limited to, eukaryotic and prokaryotic cells, including mammalian cells known to the art.

The sample (e.g., tissue or cell culture, for example) is typically contacted with a test agent for a time period sufficient to inhibit the activity of FoxM1 or expression from a FoxM1 responsive promoter (using FoxM1 as an example transcription factor). This time period and the quantity of sample may vary depending on factors including, but not limited to, the nature of the inhibitor, the activity/expression detection mechanism and the sample tissue selected. The skilled artisan without undue experimentation may readily determine such times and amounts. An exemplary test agent is one that binds to or otherwise decreases the activity or expression of FoxM1, although test agents that inhibit the activity or expression by, for example, binding to a component of a signal pathway leading to FoxM1 expression, such as an enzyme substrate, or by some other mechanism, are also envisioned. When a sample tissue or particular cell type is used, the type of tissue or cell chosen may vary depending on the specific cancer being studied. Nonlimiting examples of sample tissues include lung, colon, liver, and breast cancer tissue. Nonlimiting examples of cell types include, for example, the U2OS clone C3 cell line (17).

Inhibiting Cell Growth and/or Proliferation, Particularly Growth and/or Proliferation of Cancer Cells In another aspect, embodiments of the invention provide methods for decreasing cancer cell proliferation. The method comprises contacting a cancer cell in vitro or in vivo with a composition comprising an agent that modulates an oncogenic transcription factor activity. One such oncogenic transcription factor is FoxM1. In one embodiment, the agent modulates the FoxM1 activity by decreasing the mRNA level of FoxM1. In yet another embodiment, the agent is selected from the group consisting of hormones, cytokines, small molecules, antibodies, antisense oligonucleotides, chemicals, and RNA inhibitors.

Treating Cancer

In another aspect, embodiments of the invention provide methods for treating a subject that has or is at risk of developing cancer. The method comprises administering to the subject a composition comprising an agent that modulates an oncogenic transcription factor activity. One such oncogenic transcription factor is FoxM1. In one embodiment, the agent decreases the protein activity or protein level of the oncogenic transcription factor. In another embodiment, the agent decreases the mRNA level of the oncogenic transcription factor. In yet another embodiment, the agent is selected from the group consisting of hormones, cytokines, small molecules, antibodies, antisense oligonucleotides, chemicals, and RNA inhibitors. In some embodiments, the subject being treated has or is at risk of developing lung cancer, prostate cancer, basal cell cancer, non-small cell cancer, anaplastic astrocytomas, glioblastomas, colon cancer, liver cancer, or breast cancer.

"Treatment", "treating" or "treated" as used herein, means preventing, reducing or eliminating at least one symptom or complication of cancer. Exemplary symptoms and/or complications of cancer include, but are not limited to, abnormal cell growth, reduced cell death, and metastasis of cancer cells from the primary tumor. These methods include administering to a subject in need thereof a composition comprising an agent that modulates the activity of FoxM1. In one embodiment, the subject is a human. In one embodiment, this comprises administering a therapeutic amount of an agent that decreases the activity of FoxM1, such as the protein activity or the protein or RNA level of FoxM1.

A "therapeutic amount" represents an amount of an agent that is capable of inhibiting or decreasing the activity or expression of a transcription factor implicated in cancer, for example FoxM1, or causing a clinically significant response. The clinical response includes an improvement in the condition treated or in the prevention of the condition. The particular dose of the agent administered according to this invention will, of course, be determined by the particular circumstances surrounding the case, including the agent administered, the particular cancer being treated and similar conditions. In some embodiments, the agent interacts with the oncogenic transcription factor. In one embodiment, the agent is an inhibitor of FoxM1. In other embodiments, the agent interacts with the oncogenic transcription factor DNA or RNA, for example FoxM1 DNA or RNA. In still other embodiments, the agent binds to or interacts with (such as by chemically modifying) an inhibitor or activator of an oncogenic transcription factor's activity or expression. By way of nonlimiting example, an agent may bind to and inhibit an activator of FoxM1 or an agent may bind to and activate an inhibitor of FoxM1 activity.

In another aspect, the invention provides a pharmaceutical composition comprising an agent that modulates an oncogenic transcription factor and a pharmaceutically acceptable carrier. One such oncogenic transcription factor is FoxM1. The pharmaceutical composition can be used for treating cancer. Nonlimiting examples of cancer that can be treated by this method include lung cancer, liver cancer, prostate cancer, colon cancer, breast cancer, non-small cell cancer, basal cell cancer, astrocytomas, or gliobastomas. The agent may be any of the agents described herein or discovered by methods described herein. In some embodiments, the agent decreases the activity or expression of FoxM1. In some embodiments, the agent interacts directly with the protein, DNA, or RNA of FoxM1. In additional embodiments, the agent interacts with an inhibitor of FoxM1 activity or expression. In still other embodiments, the agent interacts with an activator of FoxM1 activity or expression.

The agent may be administered by a wide variety of routes. Exemplary routes of administration include oral, parenteral, transdermal, and pulmonary administration. For example, the agents may be administered intranasally, intramuscularly, subcutaneously, intraperitoneally, intravaginally and any combination thereof. For pulmonary administration, nebulizers, inhalers, or aerosol dispensers may be used to deliver the therapeutic agent in an appropriate formulation (e.g., with an aerosolizing agent). In addition, the agent may be administered alone or in combination with other agents, known drugs, or treatment methods. In combination, agents may be administered simultaneously or each agent may be administered at different times. When combined with one or more known anti-cancer drugs, agents and drugs may be administered simultaneously or the agent can be administered before or after the drug(s).

In one embodiment, the agents are administered in a pharmaceutically acceptable carrier. Any suitable carrier known in the art may be used. Carriers that efficiently solubilize the agents are preferred. Carriers include, but are not limited to a solid, liquid, or a mixture of a solid and a liquid. The carriers may take the form of capsules, tablets, pills, powders, lozenges, suspensions, emulsions, or syrups. The carriers may include substances that act as flavoring agents, lubricants, solubilizers, suspending agents, binders, stabilizers, tablet disintegrating agents, and encapsulating materials.

Tablets for systemic oral administration may include excipients, as known in the art, such as calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with disintegrating agents, such as maize, starch or alginic acid, binding agents, such as gelatin, collagen, or acacia and lubricating agents, such as magnesium stearate, stearic acid, or talc.

In powders, the carrier is a finely divided solid, which is mixed with an effective amount of a finely divided agent.

In solutions, suspensions, emulsions, or syrups, an effective amount of the agent is dissolved or suspended in a carrier such as sterile water or an organic solvent, such as aqueous propylene glycol. Other compositions can be made by dispersing the inhibitor in an aqueous starch or sodium carboxymethyl cellulose solution or a suitable oil known to the art.

The agents are administered in a therapeutic amount. Such an amount is effective in treating cancer. This amount may vary, depending on the activity of the agent utilized, the location and stage of the cancer, and the health of the patient. The term "therapeutically effective amount" is used to denote treatments at dosages effective to achieve the therapeutic result sought. Furthermore, a skilled practitioner will appreciate that the therapeutically effective amount of the agent may be lowered or increased by fine-tuning and/or by administering more than one agent, or by administering an agent with another compound. Therapeutically effective amounts may be easily determined, for example, empirically by starting at relatively low amounts and by step-wise increments with concurrent evaluation of beneficial effect (e.g., reduction in symptoms).

When one or more agents or anti-cancer compounds are combined with a carrier, they may be present in an amount of about 1 weight percent to about 99 weight percent, with the remainder being composed of the pharmaceutically acceptable carrier.

Thiazole Anticancer Agents and Combination Formulations Thereof

In another aspect, embodiments provide inhibitors of oncogenic transcription factors that are thiazole antibiotics. In embodiments the thiazole antibiotic is a potent inhibitor of oncogenic transcription factor activity and/or function. In embodiments the thiazole antibiotic inhibits anchorage-independent growth but substantially does not inhibit anchorage dependent growth. In embodiments, the thiazole antibiotic induces apoptosis in transformed cells but substantially does not induce apoptosis in normal cells. In embodiments the thiazole antibiotic is useful for treating cancer in a subject.

In embodiments the thiazole antibiotic is any one or more of Siomycin A, thiostrepton, thiopeptin, sporangiomycin, nosiheptide, multhiomycin, micrococcin, and thiocillin. In embodiments the thiazole antibiotic is a derivative, a fragment and/or a derivative of a fragment of any of the foregoing. In embodiments the oncogenic transcription factor is FoxM1. In embodiments the oncogenic transcription factor is FoxM1 and the thiazole antibiotic is Siomycin A and/or thiostrepton.

In embodiments the thiazole antibiotic sensitizes cells to inducers of apoptosis. In embodiments sensitization is effectuated through proapoptotic signal transduction pathways. Proapoptotic signals in this regard may be transduced through a subset of cytokine receptors of the tumor necrosis factor (TNF) 1 family, known as death receptors (DRs). Members of the TNF receptor family are characterized by similar extracellular domains containing cysteine-rich repeats (33). The DRs also share a common intracellular domain, the death domain (DD), which confers to them the ability to induce apoptosis. By way of DD interaction, proteins of the death-inducing signaling complex (DISC) will be recruited to the receptor, and the apoptotic machinery will be activated. In parallel to this, other adaptor molecules may bind to the complex and modulate the response, some of them inducing survival. The number of known DRs has been growing since the first one was discovered, and it seems that additional receptors are yet to be discovered (for reviews, see Refs. 34-36). The Fas receptor (FasR) or CD95/APO-1, TNF receptor 1 (TNF-R1) and TRAIL receptors 1 and 2 (TRAIL-R1 or DR4, TRAIL-R2 or DR5) are members of this family of proteins (37-39). Although the four receptors share some common features in their structures, they also have specific characteristics. The FasR binds the adaptor protein FADD (40), which in turn recruits and activates procaspase-8 (38, 41). TNF-R1, however, does not bind FADD directly, but TRADD has to be engaged before FADD (42) and procaspase-8 (43) can be recruited to the receptor.

In embodiments the thiazole antibiotics sensitize cells to proapoptotic signals transduced by the aforementioned receptors. In embodiments the thiazole antibiotics sensitize cells to apoptosis induced by members of the Tumor Necrosis Factor ligand superfamily. In embodiments the TNF ligand superfamily member is any one or more of the 4-1BB ligand, B-cell activating factor, FAS ligand, Lymphotoxin, OX40L, RANKL, TRAIL, and/or TNF-alpha.

In all of the foregoing respects and as further described herein, the thiazole antibiotic is any one or more of Siomycin A, thiostrepton, thiopeptin, sporangiomycin, nosiheptide, multhiomycin, micrococcin, and thiocillin. In embodiments the thiazole antibiotic is a derivative, a fragment, and/or a derivative of a fragment of any of the foregoing. In embodiments the oncogenic transcription factor is FoxM1. In embodiments the oncogenic transcription factor is FoxM1 and the thiazole antibiotic is Siomycin A and/or thiostrepton.

In embodiments the invention provides compositions comprising a thiazole antibiotic and an inducer of apoptosis. In embodiments the compositions are pharmaceutically acceptable compositions. In embodiments the compositions are pharmaceutically acceptable compositions for treating cancer. In embodiments the compositions further comprise any one or more of a pharmaceutically acceptable carrier, diluent, and/or excipient. In embodiments the thiazole antibiotics in any one or more of Siomycin A, thiostrepton, thiopeptin, sporangiomycin, nosiheptide, multhiomycin, micrococcin and thiocillin. In embodiments in this regard the thiazole antibiotic is a derivative, a fragment and/or a derivative of a fragment of any of the foregoing. In embodiments, the inducer of apoptosis is a member of the Tumor Necrosis Factor ligand superfamily. In embodiments, the inducer of apoptosis is any one or more of the 4-1 BB ligand, B-cell activating factor, FAS ligand, Lymphotoxin, OX40L, RANKL, TRAIL and/or TNF-alpha. In embodiments the thiazole antibiotic is Siomycin A. In embodiments the thiazole antibiotic is thiostrepton. In embodiments the inducer of apoptosis is TNF-alpha.

In all of the foregoing respects and as further described herein, in embodiments the thiazole antibiotic is any one or more of Siomycin A, thiostrepton, thiopeptin, sporangiomycin, nosiheptide, multhiomycin, micrococcin, and thiocillin. In embodiments the thiazole antibiotic is a derivative, a fragment, and/or a derivative of a fragment of any of the foregoing. In embodiments the oncogenic transcription factor is FoxM1. In embodiments the oncogenic transcription factor is FoxM1 and the thiazole antibiotic is Siomycin A and/or thiostrepton.

Embodiments of the invention provide methods for determining modulation of an oncogenic transcription factor activity by a compound, comprising: providing a cell comprising (i) a first gene encoding an oncogenic transcription factor operably linked to a first transcription control unit responsive to an effector thereof, (ii) a second gene encoding a first reporter protein operably linked to a second transcriptional control unit responsive to said oncogenic transcription factor; and (iii) a third gene encoding a second reporter protein operably linked to a third transcription control unit for constitutive transcription thereof, wherein said first and second reporter proteins engender detectable signals that are distinguishable from one another; exposing said cell to said effector and measuring said first and second signals in the absence and in the presence of said compound, and from said first and second signals in the absence and the presence of said compound determining modulation of said oncogenic transcription factor activity by said compound. In embodiments in this regard, the oncogenic transcription factor is FoxM1, the second transcription control unit is responsive to FoxM1 in said cell, the first signal is bioluminescence engendered by firefly luciferase, and the second signal is bioluminescence engendered by renilla luciferase. In embodiments the cell is exposed to a level of said effector that maximizes the signal engendered by said first reporter protein and inhibition, if any, of said oncogenic transcription factor activity by said compound is determined. In embodiments the cell is exposed to a level of said effector that maximizes the signal engendered by said first reporter protein and inhibition, if any, of said oncogenic transcription factor activity by said compound is determined.

In embodiments the invention provides methods for treating a patient suffering from a cancer, comprising determining if the NF-kB and the FoxM1 oncogenic pathways are activated in said cancer, and, if both pathways are activated, administering to said patient a thiazole antibiotic by a route and in an amount effective for treating said cancer. In embodiments the thiazole antibiotic is one or more of Siomycin A, thiostrepton, thiopeptin, sporangiomycin, noiheptide, multhiomycin, micrococcin, and thiocillin. In embodiments the thiazole antibiotic is Siomycin A or thiostrepton. In embodiments the method further comprises administering to the patient a ligand that is a member of the tumor necrosis factor superfamily of ligands. In embodiments the ligand is one or more of TNF-alpha, 4-1BB ligand, B-cell activating factor, FAS ligand, Lymphotoxin, OX40L, RANKL, and TRAIL. In embodiments the ligand is TNF-alpha. In embodiments the cancer is selected from the group consisting of lung, colon, liver, breast, prostate, basal cell, non-small cell, CNS, or brain cell cancer.

In embodiments the invention provides compositions comprising a thiazole antibiotic and a ligand that is a member of the Tumor Necrosis Factor superfamily. In embodiments the thiazole antibiotic is Siomycin A, thiostrepton, thiopeptin, sporangiomycin, noiheptide, multhiomycin, micrococcin, or thiocillin and the ligand is TNF-alpha, 4-1BB ligand, B-cell activating factor, FAS ligand, Lymphotoxin, OX40L, RANKL, or TRAIL. In embodiments the thiazole antibiotic is Siomycin A or thiostrepton and the ligand is TNF-alpha. In embodiments the composition further comprises a pharmaceutically acceptable carrier.

Embodiments of the invention provide as well a high throughput assay for rapidly screening a plurality of compounds to determine the degree of modulation of an oncogenic transcription factor activity by the compounds, the assay comprising: (a) providing a cell engineered to express an oncogenic transcription factor-reporter fusion protein from an inducible promoter; wherein the cell further comprises a first reporter gene operatively associated with a promoter which is responsive to the oncogenic transcription factor; and wherein the cell further comprises a second reporter gene operatively associated with a constitutive promoter; (b) contacting a compound from the plurality of compounds with the cell and assaying a level of expression from the oncogenic transcription factor responsive promoter; and (c) identifying a compound that decreases the expression level from the oncogenic transcription factor responsive promoter while not substantially affecting expression of the second reporter gene from the constitutive promoter. In embodiments each of the reporter protein, the first reporter gene, and the second reporter gene encode different reporter products relative to each other.

In embodiments the invention provides a method for decreasing cell proliferation, comprising contacting a cell in vitro with a composition comprising an agent that modulates FoxM1 activity. In embodiments the agent is selected from the group consisting of hormones, cytokines, small molecules, antibodies, antisense oligonucleotides, chemical, and RNA inhibitors. In embodiments the agent is a small molecule is selected from the group consisting of Siomycin A and Thiostrepton. In embodiments the oncogenic transcription factor is FoxM1.

BRIEF DESCRIPTION OF THE FIGURES

FIG. 12. Thiazole antibiotics inhibit the growth of human cancer cells. Breast (A), liver (B) cancer and leukemia (C) cell lines were treated with different concentrations of Siomycin A and thiostrepton for 48 hrs and growth inhibition was assessed by cell count.

DESCRIPTION OF THE INVENTION

Figure 1:
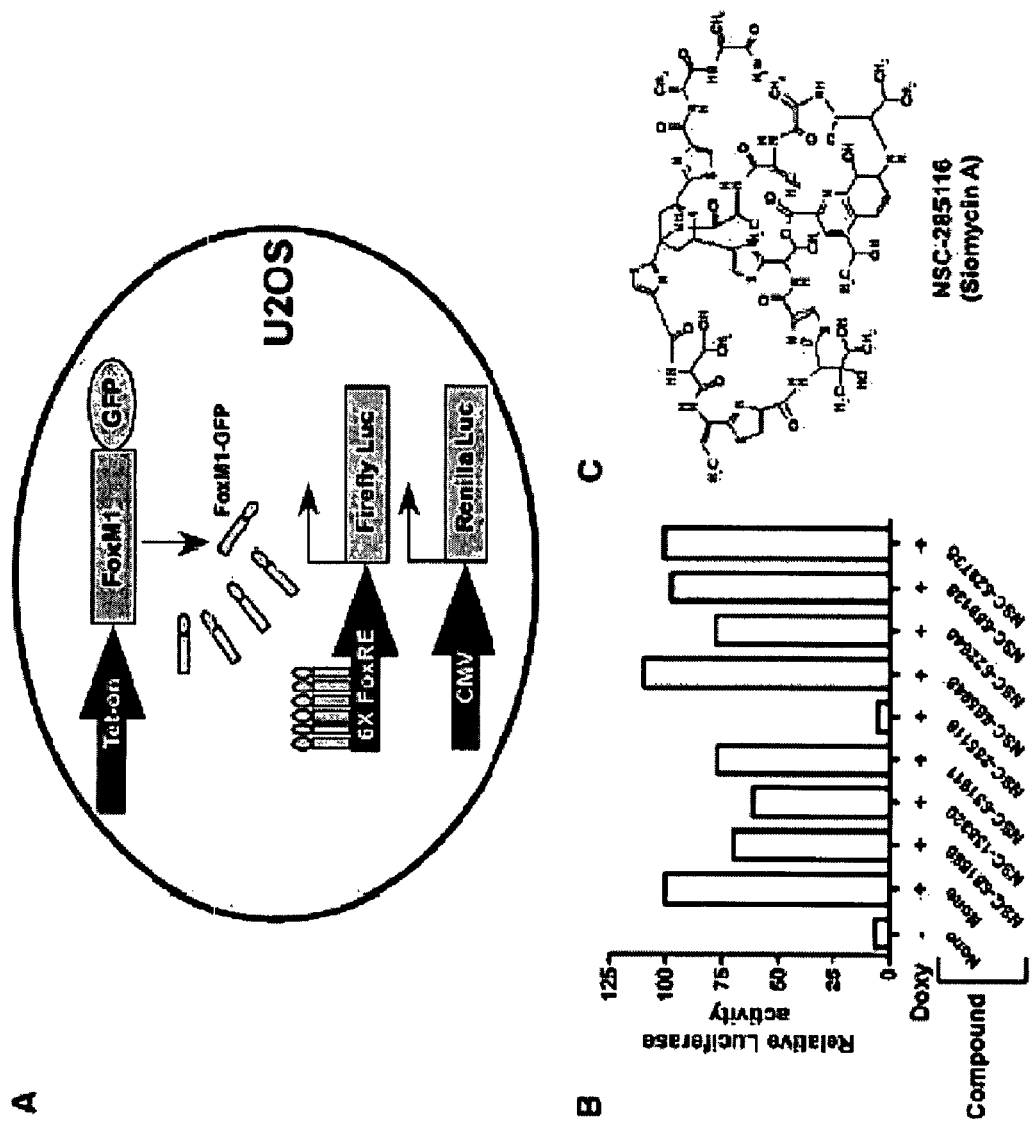
FIG. 1. Identification of an inhibitor of FoxM1 transcriptional activity. (A) The C3-Luc cell line was derived from U2OS cells as described in the Materials and Methods. These cells were used for screening against the library of compounds from the National Cancer Institute. (B) Part of the screening data containing the positive hit (NSC-285116; Siomycin A) is shown. Compounds were tested at a final concentration of 10 μM. (C) Chemical structure of the antibiotic thiazole compound Siomycin A is shown.

The present invention relates to methods for molecular investigations of transcription factors implicated in cancer, to methods for screening for agents that modulate their activity, to the formulation of these agents and to their use, alone and in combination with other agents to treat disease, as described in greater detail herein. In embodiment the diseases are cancers. In embodiments the cancers are those in which both the FoxM1 and NF-kβ pathways of oncogenesis are activated. In embodiments the agent is a modulator of oncogenic transcription factor. In embodiments the agent is an inhibitor of an oncogenic transcription factor. In embodiments the oncogenic transcription factor is FoxM1. In embodiments the agents are thiazole antibiotics. In embodiments the thiazole antibiotics are one or both of Siomycin A and thiostrepton. In embodiments a thiazole antibiotic is used in combination with an inducer of apoptosis. In embodiments the inducer of apoptosis is a member of the Tumor Narcosis Factor ligand superfamily. In embodiments the inducer is TNF-alpha. In embodiments the invention provides compositions comprising an inhibitor of an oncogenic transcription factor and an inducer of apoptosis. In particular embodiments in this regard, the inhibitor is a thiazole antibiotic, such as Siomycin A and thiostrepton. In embodiments further in this regard the inducer of apoptosis is a member of the TNF ligand superfamily, such as, TNF-alpha. In embodiments the invention provides cancer treatments comprising administering to a subject an inhibitor of an oncogenic transcription factor, such as those mentioned above. In embodiment further in this regard the treatments additionally comprise administering an inducer of apoptosis, such as those mentioned above.

In certain aspects and embodiments the invention provides methods for screening the ability of compounds to modulate, in particular embodiments to inhibit, the activity of oncogenic transcription factors. In embodiments, in this regard and others, the invention provides a cell line expressing a transcription factor in an inducible system, and a first reporter under the control of a promoter which is responsive to the transcription factor of interest. As a control to select against compounds toxic to the cells and general transcriptional and/or translational inhibitors, the system may comprise a second reporter controlled by a constitutive promoter. This system can be used in a high throughput fashion for screening inhibitors that repress expression of the first reporter, but not the second.

The foregoing few paragraphs provides only a very brief and incomplete overview of some highlights of the invention, which is illustrated in greater breadth and depth by the more extensive and more detailed description below.

A. DEFINITIONS

Unless defined otherwise, all technical and scientific terms used herein have the same meanings as commonly understood by one of skill in the art to which the disclosed invention belongs.

Where ever used in this disclosure, unless otherwise clearly indicate, "a," "an," and "the" are used inclusively of the plural reference. For example, reference to "a host cell" includes two or more host cells, a multiplicity of host cells and a plurality of host cells.

As used herein, a nucleotide sequence is "operably linked" to another nucleotide sequence when it is placed in a functional relationship with another nucleotide sequence. For example, if a coding sequence is operably linked to a promoter sequence, this generally means that the promoter may modulate (e.g., promote) transcription of the coding sequence, or if a ribosome binding site is operably linked to a coding sequence, this generally means that it is positioned so as to facilitate translation. "Operably linked" means that the DNA sequences being linked are typically contiguous and, where necessary to join two protein coding regions, contiguous and in reading frame. However, since enhancers may function when separated from the promoter by several kilobases and intron sequences may be of variable lengths, some nucleotide sequences may be operably linked but not contiguous or not in reading frame. In some embodiments, linking can be accomplished by ligation at convenient binding sites, or if such sites do not exist, synthetic oligonucleotide adaptors or linkers can be used in accord with conventional practice.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. The polynucleotide can be a sequence whose presence or expression in a cell alters the expression or function of cellular genes or RNA. A delivered polynucleotide can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

Polynucleotides may contain an expression cassette coded to express a whole or partial protein, or RNA. An expression cassette refers to a natural or recombinantly produced polynucleotide that is capable of expressing a sequence. The cassette contains the coding region of the gene of interest along with any other sequences that affect expression of the sequence of interest. An expression cassette typically includes a promoter (allowing transcription initiation), and a transcribed sequence. Optionally, the expression cassette may include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences. The polynucleotide may contain sequences that do not serve a specific function in the target cell but are used in the generation of the polynucleotide.

Such sequences include, but are not limited to, sequences required for replication or selection of the polynucleotide in a host organism.

A polynucleotide can be delivered to a cell to study gene function. Delivery of a polynucleotide to a cell can also have potential clinical applications. Clinical applications include treatment of muscle disorders or injury, circulatory disorders, endocrine disorders, immune modulation and vaccination, and metabolic disorders (Baumgartner et al. 1998, Blau et al. 1995, Svensson et al. 1996, Baumgartner et al. 1998, Vale et al. 2001, Simovic et al. 2001).

A transfection agent, or transfection reagent or delivery vehicle, is a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, polycations, histone proteins, polyethylenimine, polylysine, and polyampholyte complexes. For delivery in vivo, complexes made with sub-neutralizing amounts of cationic transfection agent may be preferred. Non-viral vectors include protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers).

The term naked nucleic acids indicates that the nucleic acids are not associated with a transfection reagent or other delivery vehicle that is required for the nucleic acid to be delivered to a target cell.

"Inhibit" or "down-regulate" means that the expression of a target gene, or level of RNAs or equivalent RNAs encoding one or more proteins or isoforms, or activity of one or more proteins, is reduced below that observed in the absence of the nucleic acid molecules of the invention.

By "up-regulate" is meant that the expression of the gene, or level of RNAs or equivalent RNAs encoding one or more proteins or isoforms, or activity of one or more proteins, such as an inhibitor of FoxM1, is greater than that observed in the absence of the nucleic acid molecules of the invention. For example, the expression of a target gene can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more protein subunits, or activity of one or more proteins or protein isoforms is up-regulated or down-regulated, such that the expression, level, or activity is greater than or less than that observed in the absence of the nucleic acid molecules of the invention.

By "gene" it is meant a nucleic acid that encodes an RNA, for example, nucleic acid sequences including but not limited to structural genes encoding a polypeptide.

"Complementarity" refers to the ability of a nucleic acid to form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art (see, e.g., Turner et al., 1987, CSH Symp. Quant. Biol. LII pp. 123 133; Frier et al., 1986, Proc. Nat. Acad. Sci. USA 83:9373 9377; Turner et al., 1987, J. Am. Chem. Soc. 109:3783 3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

By "RNA" is meant a molecule comprising at least one ribonucleotide residue. By "ribonucleotide" or "2'-OH" is meant a nucleotide with a hydroxyl group at the 2' position of a β-D-ribo-furanose moiety.

"Screenable markers" as used herein include Green Fluorescent Protein (GFP), renilla luciferase, and firefly luciferase. Further examples of screenable markers are well known to one of ordinary skill in the art.

As used herein, the term "vector" refers to a nucleic acid molecule capable of transporting another nucleic acid to which it has been linked. One type of a vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g. bacterial vectors having a bacterial origin of replication and episomal mammalian vectors. Other vectors (e.g. non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form plasmids. In the present specification, "plasmid" and "vector" can be used interchangeably as the plasmid is the most commonly used from of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which are operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein or RNA desired, etc. The expression vectors of the invention can be introduced into host cells to thereby produce siNAs, RNAs, proteins or peptides, including fusion proteins or peptides.

In another embodiment, a nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the albumin promoter, lymphoid-specific promoters, neuron specific promoters, pancreas specific promoters, and mammary gland specific promoters. Developmentally-regulated promoters are also encompassed, for example, the murine hox promoters and the α-fetoprotein promoter.

In another aspect the nucleic acid molecules comprise a 5' and/or a 3'-cap structure. By "cap structure" is meant chemical modifications, which have been incorporated at either terminus of the oligonucleotide (see for example Wincott et al, WO 97/26270, incorporated by reference herein). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted a basic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT Publication No. WO 97/26270, incorporated by reference herein).

In another embodiment the 3'-cap includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925, incorporated by reference herein).

The administration of the herein described agents to a patient can be intravenous, intraarterial, intraperitoneal, intramuscular, subcutaneous, intrapleural, intrathecal, by perfusion through a regional catheter, or by direct intralesional injection. When administering these nucleic acid molecules by injection, the administration may be by continuous infusion, or by single or multiple boluses. The dosage of the administered agent will vary depending upon such factors as the patient's age, weight, sex, general medical condition, and previous medical history. Typically, it is desirable to provide the recipient with a dosage of a nucleic acid agent which is in the range of from about 1 pg/kg to 10 mg/kg (amount of agent/body weight of patient), although a lower or higher dosage may also be administered.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18$^{th}$ Ed. (1990).

For purposes of immunotherapy, an immunoconjugate and a pharmaceutically acceptable carrier are administered to a patient in a therapeutically effective amount. A combination of an immunoconjugate and a pharmaceutically acceptable carrier is said to be administered in a "therapeutically effective amount" if the amount administered is physiologically significant. An agent is physiologically significant if its presence results in a detectable change in the physiology of a recipient patient.

Additional pharmaceutical methods may be employed to control the duration of action of an immunoconjugate in a therapeutic application. Control release preparations can be prepared through the use of polymers to complex or adsorb an immunoconjugate. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446-1449 (1992). The rate of release of an agent from such a matrix depends upon the molecular weight of the molecule, the amount of molecule within the matrix, and the size of dispersed particles. Saltzman et al., Biophysical. J. 55:163-171 (1989); and Sherwood et al., *Bio/Technology* 10:1446-1449 (1992). Other solid dosage forms are described in REMINGTON'S PHARMACEUTICAL SCIENCES, 18th Ed. (1990).

B. SCREENING SYSTEMS AND METHODS OF TREATMENT

One aspect of the invention provides a method for treating a subject that has or is at risk of developing cancer. The method comprises administering to the subject a composition comprising an agent that modulates an oncogenic transcription factor activity. In one embodiment, the agent decreases the protein activity or protein level of the oncogenic transcription factor. In another embodiment, the agent decreases the mRNA level of the oncogenic transcription factor. In yet another embodiment, the oncogenic transcription factor is FoxM1. In yet another embodiment, the agent is selected from the group consisting of hormones, cytokines, small molecules, antibodies, antisense oligonucleotides, chemicals, and RNA inhibitors. In some embodiments, the subject being treated has or is at risk of developing lung cancer, prostate cancer, basal cell cancer, non-small cell cancer, anaplastic astrocytomas, glioblastomas, colon cancer, liver cancer, or breast cancer.

In another aspect of the present invention, a method is provided for screening for an agent that modulates that activity of an oncogenic transcription factor such as FoxM1. The method comprises exposing a sample to an agent to be tested, detecting a level of activity of the oncogenic transcription factor and comparing the level of activity of the oncogenic transcription factor to a control level. In one embodiment, the oncogenic transcription factor activity detected and compared is the promoter activity wherein a reporter construct containing a promoter which is responsive to the oncogenic transcription factor is used. An example of an oncogenic transcription factor that can be used in the methods described herein is FoxM1. In another embodiment, and as a control to select against compounds toxic to the sample and general transcriptional and/or translational inhibitors, the method may comprise a second reporter controlled by a constitutive promoter. This system can be used in a high throughput fashion for screening inhibitors that repress expression of the first reporter, but not the second. The sample may be of tissue or cell culture, for example.

In another aspect, the invention provides a method for decreasing cancer cell proliferation. The method comprises contacting a cancer cell in vitro or in vivo with a composition comprising an agent that modulates an oncogenic transcription factor activity. In one embodiment, the agent modulates FoxM1 activity, for example, by decreasing the mRNA level of FoxM1. In another embodiment, the agent is selected from the group consisting of hormones, cytokines, small molecules, antibodies, antisense oligonucleotides, chemicals, and RNA inhibitors.

The oncogenic transcription factor, FoxM1 for example, may be produced by methods known to the skilled artisan. For example, a nucleotide sequence encoding the FoxM1 gene may be introduced into a desired host cell. Such a nucleotide sequence may first be inserted into an appropriate recombinant expression vector.

Recombinant expression vectors may be constructed by incorporating nucleotide sequences within a vector according to methods well known to the skilled artisan. A wide variety of vectors are known that are useful in the invention. Suitable vectors include plasmid vectors and viral vectors, including retrovirus vectors, adenovirus vectors, adeno-associated virus vectors and herpes viral vectors. The vectors may include other known genetic elements necessary or desirable for efficient expression of the nucleic acid in a specified host cell, including regulatory elements. For example, the vectors may include a promoter and any necessary enhancer sequences that cooperate with the promoter to achieve transcription of the gene. The nucleotide sequence may be operably linked to such regulatory elements.

Such a nucleotide sequence is referred to as a "genetic construct." A genetic construct may contain a genetic element on its own or in combination with one or more additional genetic elements, including but not limited to genes, promoters, or enhancers. In some embodiments, these genetic elements are operably linked. In some embodiments, the specific gene at issue (e.g., FoxM1) may not be present in the genetic construct, including, but not limited to, a situation in which a FoxM1 responsive promoter is operably linked to a reporter gene. It is possible to modify the screening system to identify inhibitors that affect transcriptional activity of the oncogenic transcription factor of interest, that affect the mRNA levels of the oncogenic transcription factor of interest, and/or that affect the protein levels of the oncogenic transcription factor of interest. Such modifications are well within the skill level of one of ordinary skill in the art. Transcriptional fusions and translational fusions are well known genetic constructs which can be used in any of the methods described herein.

C. POTENT INHIBITERS OF ONCOGENIC TRANSCRIPTION FACTORS AND ENHANCED APOPTOTIC EFFECTS ON CANCER CELLS IN COMBINATION WITH INDUCERS OF APOPTOSIS

In another aspect, embodiments provide inhibitors of oncogenic transcription factors. Such factors may be proteins or peptides or derivatives thereof, anti-sense reagents, and "small organic molecules" to name a few examples. They may be hormones, cytokines, antibodies or antibody-derived proteins. They may be antisense RNAs or DNAs, including oligonucleotides and longer polynucleotides and derivatives thereof. They may be "small organic molecules" such as ligands, inhibitors, and the like.

Among inhibitors of oncogenic transcription factors in embodiments of the invention are thiazole antibiotics. In embodiments the thiazole antibiotic is a potent inhibitor of oncogenic transcription factor activity and/or function. In embodiments the thiazole antibiotic inhibits anchorage-independent growth but substantially does not inhibit anchorage dependent growth. In embodiments, the thiazole antibiotic induces apoptosis in transformed cells but substantially does not induce apoptosis in normal cells. In embodiments the thiazole antibiotic is useful for treating cancer in a subject.

In embodiments the thiazole antibiotic is any one or more of Siomycin A, thiostrepton, thiopeptin, sporangiomycin, nosiheptide, multhiomycin, micrococcin and thiocillin. In embodiments the thiazole antibiotic is a derivative, a fragment and/or a derivative of a fragment of any of the foregoing. In embodiments the oncogenic transcription factor is FoxM1. In embodiments the oncogenic transcription factor is FoxM1 and the thiazole antibiotic is Siomycin A and/or thiostrepton.

In embodiments the thiazole antibiotic sensitizes cells to inducers of apoptosis. In embodiments sensitization is effectuated through proapoptotic signal transduction pathways. Proapoptotic signals in this regard may be transduced through a subset of cytokine receptors of the tumor necrosis factor (TNF) 1 family, termed death receptors (DRs). Members of the TNF receptor family are characterized by similar extracellular domains containing cysteine-rich repeats (33). The DRs also share a common intracellular domain, the death domain (DD), which confers to them the ability to induce apoptosis. By way of DD interaction, proteins of the death-inducing signaling complex (DISC) will be recruited to the receptor, and the apoptotic machinery will be activated. In parallel to this, other adaptor molecules may bind to the complex and modulate the response, some of them inducing survival. The number of known DRs has been growing since the first one was discovered, and it seems that additional receptors are yet to be discovered (for reviews, see Refs. 34-36). The Fas receptor (FasR) or CD95/APO-1, TNF receptor 1 (TNF-R1) and TRAIL receptors 1 and 2 (TRAIL-R1 or DR4, TRAIL-R2 or DR5) are members of this family of proteins (37-39). Although the four receptors share some common features in their structures, they also have specific characteristics. The FasR binds the adaptor protein FADD (40), which in turn recruits and activates procaspase-8 (38, 41). TNF-R1, however, does not bind FADD directly, but TRADD has to be engaged before FADD (42) and procaspase-8 (43) can be recruited to the receptor.

In embodiments the thiazole antibiotics sensitize cells to proapoptotic signals transduced by the aforementioned receptors. In embodiments the thiazole antibiotics sensitize cells to apoptosis induced by members of the Tumor Necrosis Factor ligand superfamily. In embodiments the TNF ligand superfamily member is any one or more of the 4-1BB ligand, B-cell activating factor, FAS ligand, Lymphotoxin, OX40L, RANKL, TRAIL, and/or TNF-alpha.

In all of the foregoing respects and as further described herein, the thiazole antibiotic is any one or more of Siomycin A, thiostrepton, thiopeptin, sporangiomycin, nosiheptide, multhiomycin, micrococcin, and thiocillin. In embodiments the thiazole antibiotic is a derivative, a fragment, and/or a derivative of a fragment of any of the foregoing. In embodiments the oncogenic transcription factor is FoxM1. In embodiments the oncogenic transcription factor is FoxM1 and the thiazole antibiotic is Siomycin A and/or thiostrepton.

In embodiments the invention provides compositions comprising a thiazole antibiotic and an inducer of apoptosis. In embodiments the compositions are pharmaceutically acceptable compositions. In embodiments the compositions are pharmaceutically acceptable compositions for treating cancer. In embodiments the compositions further comprise any one or more of a pharmaceutically acceptable carrier, diluent, and/or excipient. In embodiments the thiazole antibiotics in any one or more of Siomycin A, thiostrepton, thiopeptin, sporangiomycin, nosiheptide, multhiomycin, micrococcin, and thiocillin. In embodiments in this regard the thiazole antibiotic is a derivative, a fragment and/or a derivative of a fragment of any of the foregoing. In embodiments, the inducer of apoptosis is a member of the Tumor Necrosis Factor ligand superfamily. In embodiments, the inducer of apoptosis is any one or more of the 4-1 BB ligand, B-cell activating factor, FAS ligand, Lymphotoxin, OX40L, RANKL, TRAIL, and/or TNF-alpha. In embodiments the thiazole antibiotic is Siomycin A. In embodiments the thiazole antibiotic is thiostrepton. In embodiments the inducer of apoptosis is TNF-alpha.

In all of the foregoing respects and as further described herein, in embodiments the thiazole antibiotic is any one or more of Siomycin A, thiostrepton, thiopeptin, sporangiomycin, nosiheptide, multhiomycin, micrococcin, and thiocillin. In embodiments the thiazole antibiotic is a derivative, a fragment, and/or a derivative of a fragment of any of the foregoing. In embodiments the oncogenic transcription factor is FoxM1. In embodiments the oncogenic transcription factor is FoxM1 and the thiazole antibiotic is Siomycin A and/or thiostrepton.

A particular illustration in this regard is Siomycin A, which we show is a potent inhibitor of FoxM1 activity, engenders apoptosis in cancer cells, greatly potentates the apoptotic effects of TNF-alpha on these cells and is an effective agent for inhibiting the growth and engendering cell death of human cancer cells in model systems, particularly when used in combination with TNF-alpha. Notably, Siomycin A inhibits anchorage-independent growth and induces apoptosis in transformed, but not normal cells. These anti-cancer properties of Siomycin A are consistent with an earlier report where it was identified in a screen for pro-apoptotic compounds using a human breast cancer MDA-MB-231 cell line in an ELISA assay that specifically recognizes caspase-cleaved cytokeratin 18 (26). Furthermore, another study indicated that Siomycin A induced Endoplasmic reticulum stress, and lysosomal membrane permeabilization followed by cell death in HCT116 colon cancer cells (27). Though p53 was induced due to Siomycin A treatment in these cells, apoptosis was found to be p53-independent. Interestingly, Siomycin A is a part of the NCI's *Challenge Set*, in which the compounds exhibit unusual patterns of cell sensitivity and resistance, but through currently unknown mechanisms (28). The foregoing data is consistent with the hypothesis that negative regulation of FoxM1 function and expression by Siomycin A at least partly contributes to the anti-cancer and pro-apoptotic activity of this antibiotic.

EXAMPLES

The following Examples, which further illustrate certain embodiments of the invention, are provided by way of exemplification only and are not in any way limitative of the overall scope of the invention or of its embodiments.

Example 1

Materials and Methods

The following materials and methods were used in carrying out examples described below.

Screening System

The development of U2OS clone C3 cell line with doxycyclin inducible FoxM1-GFP fusion protein has been described before (17). This cell line was transfected with a plasmid expressing firefly luciferase under the control of 6× FoxM1 responsive (FoxRE) promoter (17), along with pcDNA3.1 (Invitrogen, Carlsbad, Calif.) plasmid that expresses neomycin phospho-transferase. The resultant cells were selected in 800 µg/ml G418 (Invitrogen, Carlsbad, Calif.) and a single resistant clone that showed several fold Doxycycline-dependent induction in firefly luciferase activity was expanded. This clone was further transfected with pRL-CMV (Promega) that expresses renilla luciferase along with pLPCX-puro (Clontech), and the cells were selected in 2 µg/ml puromycin. This cell line which expresses FoxM1-dependent firefly luciferase and constitutive renilla luciferase was named as C3-Luc and used for the screening of compound libraries (Challenge set and Diversity set) from the National Cancer Institute.

Luciferase Assays

For high-throughput screening, the C3-Luc cells were grown in 96-well plates and treated overnight with a combination of 1 µg/ml doxycycline and 10 µM of compounds from the library. Next day, the firefly and renilla luciferase activities were measured with the Dual Glo system (E2940; Promega).

For the other luciferase assay experiments, the cells were treated as indicated in the FIG. 1 legend and the luciferase activity was measured using the Dual Luciferase reporter assay system (E1910; Promega) according to the manufacturer's instructions.

Real-Time Quantitative Reverse Transcription PCR (RT-PCR)

Cells treated with Siomycin A or DMSO (control) were harvested 24 hrs later and RNA was extracted using the TRIzol reagent (15596-026; Invitrogen). cDNA was prepared from this RNA using the Bio-Rad cDNA synthesis kit. The following sense (S) and antisense (AS) primer sequences and annealing temperatures (Ta) were used to amplify and measure the amount of human mRNA by real-time RT-PCR: FoxM1-S, 5'-GGA GGA AAT GCC ACA CTT AGC G-3' (SEQ ID NO: 1), and FoxM1-AS, 5'-TAG GAC TTC TTG GGT CTT GGG GTG-3' (SEQ ID NO: 2) (Ta, 55.7° C.); survivin-S, 5'-TCA AGG ACC ACC GCA TCT CTA-3' (SEQ ID NO: 3), and survivin-AS, 5'-TGA AGC AGA AGA AAC ACT GGG C-3' (SEQ ID NO: 4) (Ta, 61° C.); CENPB-S, 5'-ATT CAG ACA GTG AGG AAG AGG ACG-3' (SEQ ID NO: 5), and CENPB-AS, 5'-CAT CAA TGG GGA AGG AGG TCA G-3' (SEQ ID NO: 6) (Ta, 58° C.); Cdc25B-S, 5'-CCC TTC CCT GTT TTC CTT TC-3' (SEQ ID NO: 7), and Cdc25B-AS, 5'-ACA CAC ACT CCT GCC ATA GG-3' (SEQ ID NO: 8) (Ta, 61.7° C.). These real-time RT-PCR RNA levels were normalized to human cyclophilin mRNA levels, and these primers are as follows: cyclophilin-S, 5'-GCA GAC AAG GTC CCA AAG ACA G-3' (SEQ ID NO: 9), and cyclophilin-AS, 5'-CAC CCT GAC ACA TAA ACC CTG G-3' (SEQ ID NO: 10) (Ta, 55.7° C.).

Immunoblot Analysis and Immunoprecipitation

Immunoblotting was performed as described (18-20) with antibodies specific for p21 (556431; BD Pharmingen), survivin (sc-10811; Santa Cruz), cleaved caspase-3 (9664; Cell Signaling), and β-actin (A5441; Sigma) antibodies. Immunoblot for FoxM1 was done using the previously generated rabbit antisera (2), and phospho-FoxM1 was detected using the MPM2 monoclonal antibody (Upstate Biotechnology) which recognizes the phosphorylated protein sequence phosphoserine/phosphothreonine-proline.

For the immunoprecipitation experiment, FoxM1 antisera (2) was used along with protein A-sepharose to pull down FoxM1 protein, which was resolved on an SDS-PAGE gel and transferred to PVDF membrane. The total and phospho-FoxM1 levels were determined by using the antibodies described above.

Soft Agar Assay

The assay was done as described previously (21, 22). Briefly C3-Luc cells were plated subconfluently in six-well plates in 0.7% agarose on a 1.4% agarose bed in the presence or absence of 10 μM of Siomycin A and 1 μg/mL of doxycycline. Three times a week, the tissue-culture medium containing these agents was replaced. After 4 weeks, cell colonies that were larger than 1 mm in size were scored.

Apoptosis Assay

Apoptosis was detected by DAPI (4',6-diamidino-2-phenylindole) staining. All treatments were done in triplicates in 6-well plates and cells were stained with DAPI and visualized by fluorescent microscopy. Four random fields for each sample were photographed and at least 500 cells per field were counted to estimate apoptosis. The data is represented as mean±sd.

Example 2

Identification of Siomycin A as an Inhibitor of FoxM1

Transcriptional Activity

In order to screen for inhibitors of FoxM1 transcriptional activity in a high throughput fashion, we developed a U2OS cell line C3-Luc (described in Example 1) that stably expresses doxycycline/tetracycline-inducible FoxM1-GFP, firefly luciferase under the control of multiple FoxM1 response elements, and a renilla luciferase under the control of a CMV promoter (FIG. 1A). We first verified that when doxycycline is added to the medium, FoxM1-GFP is highly induced leading to several fold induction in firefly luciferase activity with minimal change in the renilla luciferase activity. (Data not shown.) We then used this C3-Luc cell line to screen against compounds (Challenge Set and Diversity Set) obtained from National Cancer Institute (Supplementary Table S1). We found that while the relative firefly luciferase activity was enhanced ~16-fold upon induction with doxycycline, addition of Siomycin A (NSC-285116) efficiently reduced the value to basal levels (FIG. 1B). Siomycin A is a well known antibiotic and its structure is shown in FIG. 1C. It belongs to the thiazole group, and this class of antibiotics exerts their antibacterial effect by interacting with the 23 S ribosomal RNA (23).

Figure 2:
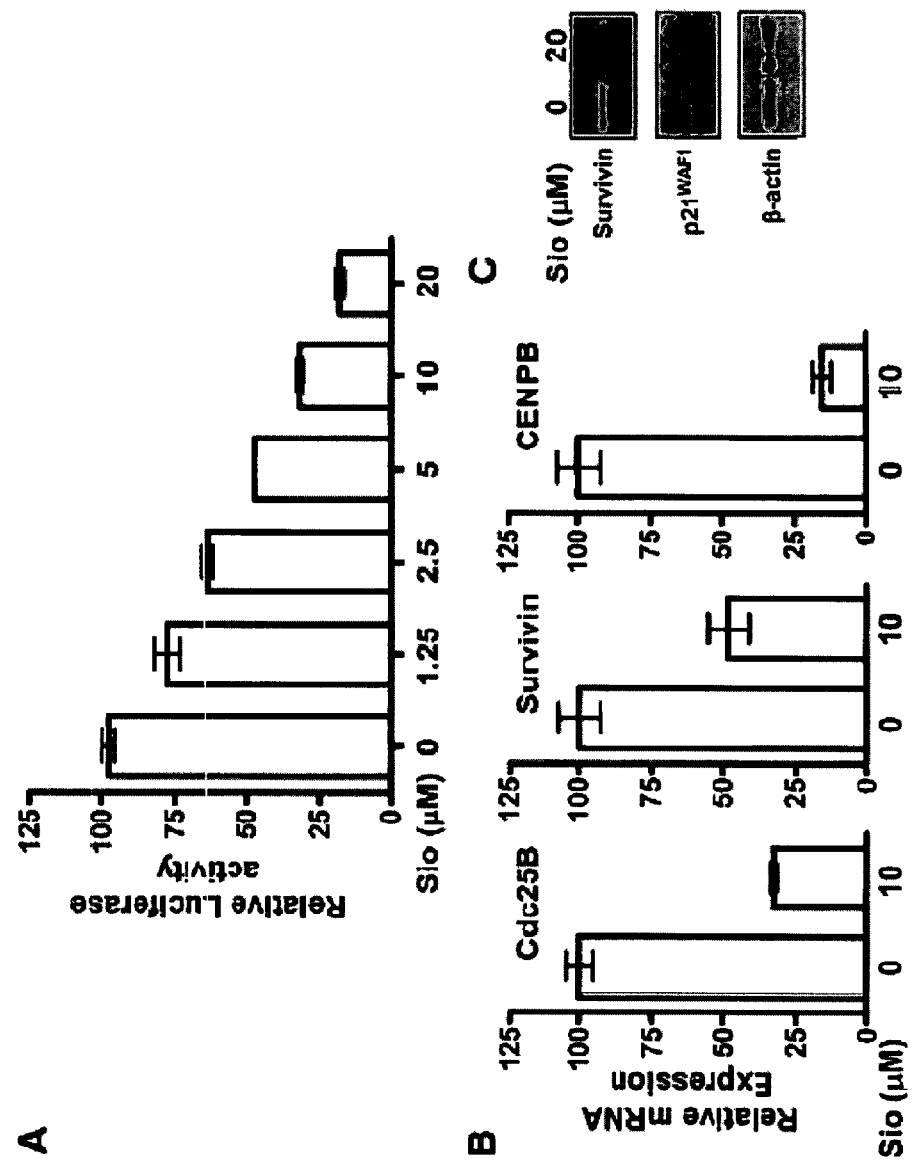
FIG. 2. Siomycin A inhibits endogenous FoxM1 transcriptional activity. (A) C3-Luc cells without doxycycline induction, were treated with increasing dose of Siomycin A and luciferase activity was determined as described in Example 1. (B) C3-Luc cells treated either with DMSO (control) or Siomycin A were harvested 24 hrs later and the RNA was subjected to real-time RT-PCR for quantitation of mRNA levels of FoxM1 target genes Cdc25B, Survivin, and CENPB. (C) C3-Luc cells treated as indicated were harvested 24 hrs later and used for immunoblot analysis to determine the levels of survivin, and $p21^{WAF1}$. β-actin protein levels were used as loading control.

Next, we wanted to investigate if Siomycin A can inhibit the transcriptional activity of endogenous FoxM1. To this end, we treated the C3-Luc cells (without doxycycline induction) with increasing concentration of Siomycin A and found a dose-dependent decrease in the firefly luciferase activity conferred by the FoxM1-responsive promoter (FIG. 2A; Supplementary Table S2). In addition, using quantitative Real-time PCR we found that the mRNA levels of the transcriptional targets of FoxM1 were inhibited in C3-Luc cells upon treatment with Siomycin A (FIG. 2B). While Cdc25B was reduced to 32% of its basal value, Survivin and CENPB were reduced to 48% and 15%, respectively, compared to their initial levels, after Siomycin A treatment (FIG. 2B). Also, protein levels of survivin were dramatically reduced in the presence of Siomycin A (FIG. 2C). Since FoxM1 transcriptionally induces Skp2 and Cks1, which degrade $p21^{WAF1}$ protein (2), an inhibitor of FoxM1 should increase $p21^{WAF1}$ protein levels. Accordingly, immunoblotting for $p21^{WAF1}$ revealed an increase in its protein levels after treatment with Siomycin A (FIG. 2C). Taken together, these data suggest that Siomycin A is capable of inhibiting both exogenous and endogenous FoxM1 transcriptional activity (FIGS. 1 and 2).

Example 3

Mechanism of FoxM1 Inhibition by Siomycin A

Figure 3:
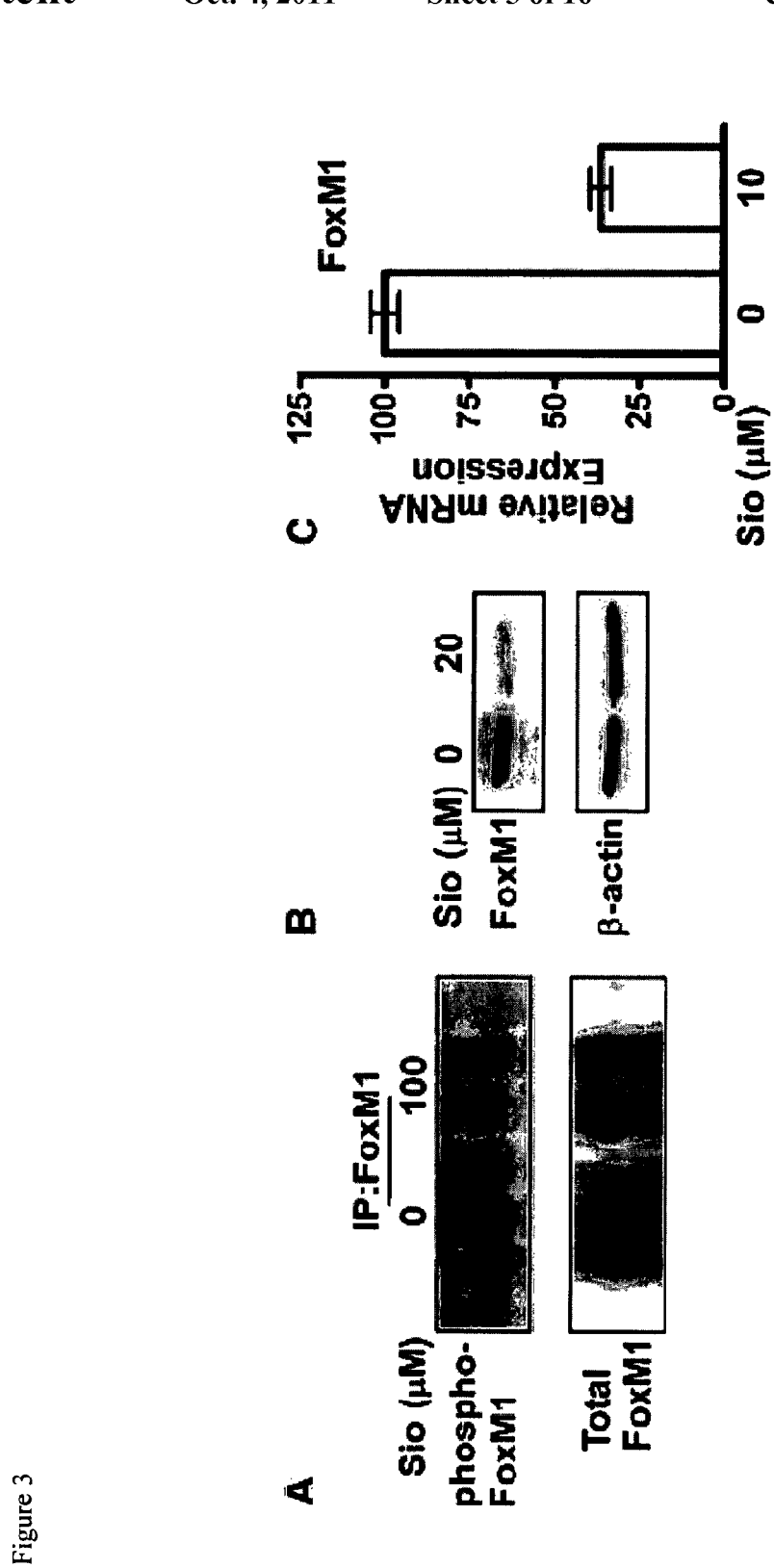
FIG. 3. Mechanisms of FoxM1 inhibition by Siomycin A. (A) C3-Luc cells treated as indicated were harvested after 8 hrs and cell lysates were used for immunoprecipitation of FoxM1 protein. These samples were resolved on an SDS-PAGE gel and immunoblotted to determine total and phospho-FoxM1 levels. (B) C3-Luc cells treated with Siomycin A or DMSO were harvested 24 hrs later and the lysates were used to determine FoxM1 protein levels by immunoblotting. (C) RNA from C3-Luc cells treated with Siomycin A or DMSO for 24 hrs was used to determine levels of FoxM1 mRNA using real-time quantitative RT-PCR.

Previously it has been demonstrated that cdk1/2-dependent phosphorylation of FoxM1 on Thr596 resulting in p300/CBP recruitment, is essential for the transcriptional activity of FoxM1 (22). Based on this observation, we hypothesized that Siomycin A may inhibit FoxM1 transcriptional activity by blocking this phosphorylation event. In order to test this hypothesis, we treated C3-Luc cells with DMSO (control) or 100 μM of Siomycin A for 8 hrs and immunoprecipitated FoxM1 from the lysates. We then analyzed these samples for phospho-FoxM1 levels by immunoblotting with MPM2, a monoclonal antibody that recognizes phosphorylated Cdk1 and Cdk2 sites. We found that Siomycin A treatment led to a decrease in phospho-FoxM1, while the total FoxM1 levels were only marginally reduced (FIG. 3A). We also found that prolonged treatment of C3-Luc cells for 24 hrs with Siomycin A significantly decreased FoxM1 protein and mRNA levels (FIG. 3B, FIG. 3C). These data imply that Siomycin A antagonizes FoxM1 function by at least two distinct mechanisms—one by blocking its phosphorylation thereby leading to its reduced transactivation ability and the other by down-regulating its mRNA and protein levels.

Example 4

Anti-Cancer Properties of FoxM1 Inhibitor Siomycin A

In a previous study, it has been shown that inhibiting FoxM1 using an ARF-derived peptide leads to a decrease in anchorage-independent growth of U2OS cells on soft agar (17). In order to test if Siomycin A could recapitulate this effect, we performed a clonogenic assay, wherein we grew the C3-Luc cells with or without FoxM1 induction and Siomycin treatment for 4 weeks. We found that while induction of FoxM1 led to a 2-fold increase in the number of colonies, addition of Siomycin A dramatically reduced the anchorage-independent growth to less than basal untreated value (FIG.

4A, 4B). This result suggests that Siomycin A may act as an effective inhibitor of FoxM1-based cellular transformation.

Figure 4:
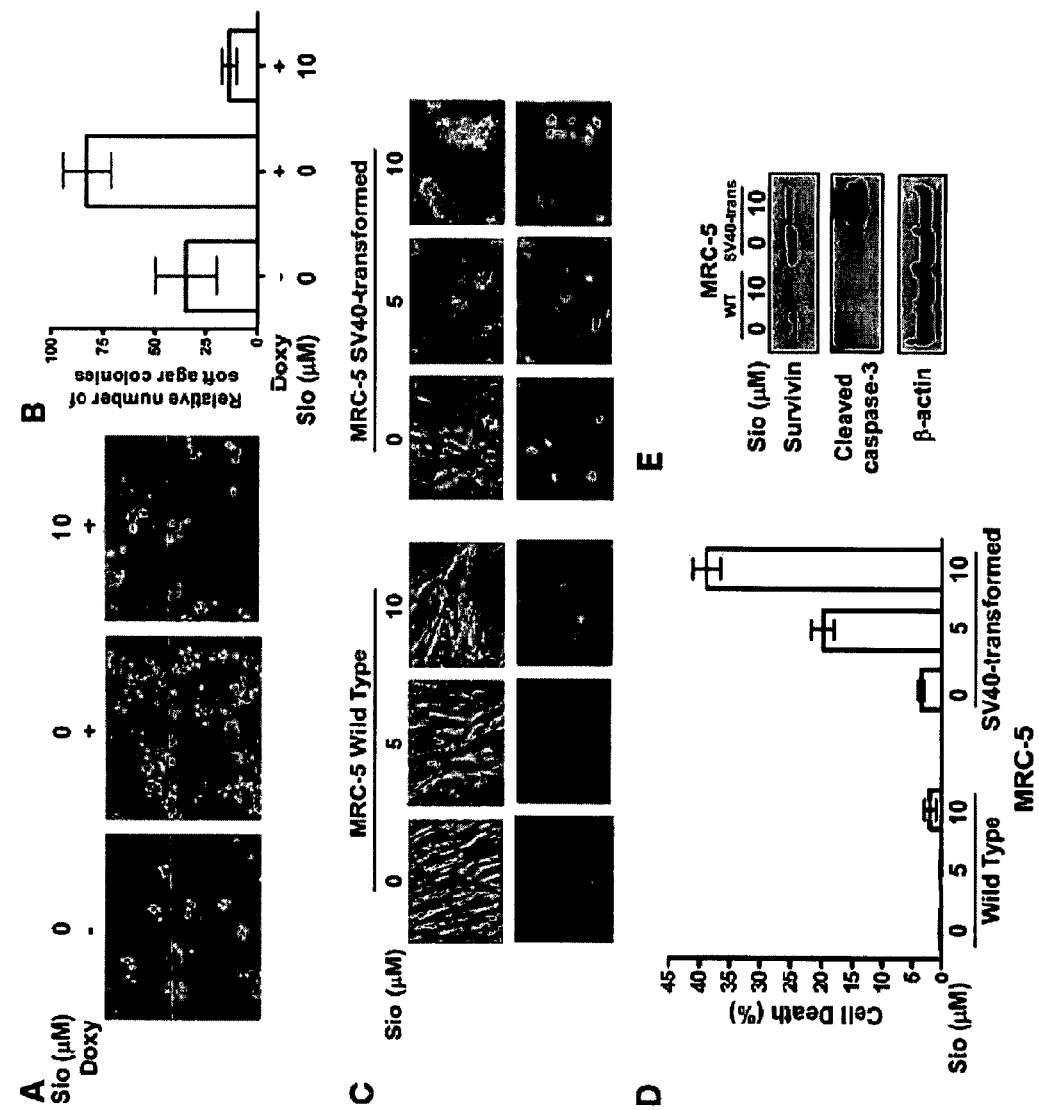
FIG. 4. Anti-cancer properties of Siomycin A. (A) Representative photographs from soft agar experiment as described in Example 1 are shown. (B) Number of colonies in the soft agar were quantitated and plotted in the form of bar graphs. (C) Wild type and SV40-transformed MRC-5 human fetal lung fibroblasts were treated with indicated concentrations of Siomycin A for 48 hrs. Photographs from phase contrast microscopy (top panel) and fluorescent microscopy after DAPI staining (bottom panel) are shown. (D) Apoptotic nuclei from normal and SV40-transformed MRC-5 fibroblasts treated with indicated concentrations of Siomycin A for 24 hrs were scored after DAPI staining and percentage cell death (mean±sd; n=3) is shown. (E) Wild type and SV40-transformed MRC-5 fibroblasts were treated with Siomycin A as indicated for 48 hrs and the cell lysates were used for immunoblotting and probed for levels of survivin and cleaved caspase-3.
Figure 5:
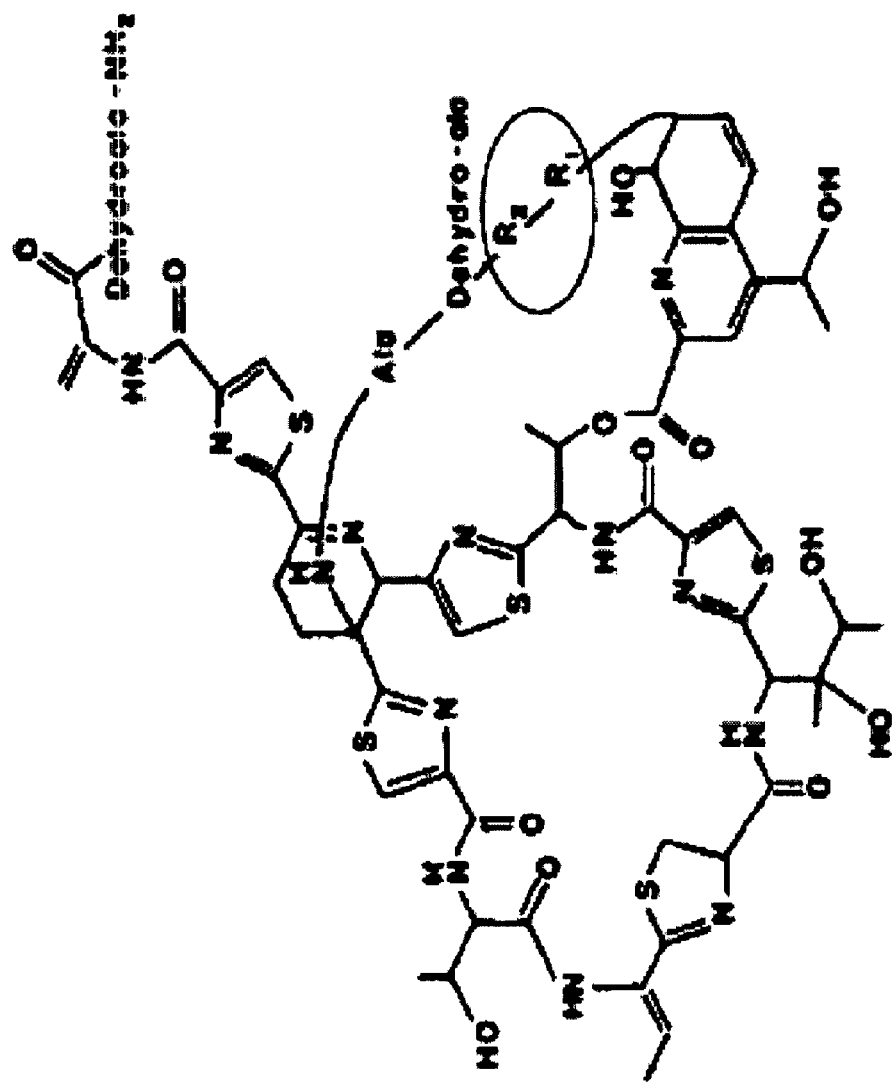
FIG. 5. Chemical Structures of thiostrepton and Siomycin A (Thiostrepton-$R_1$-$R_2$: Isoleucine-alanine; Siomycin-$R_1$-$R_2$: valine-dehydroalanine).

In order to further test the anti-cancer properties of Siomycin A and to see if it has any specificity towards transformed cells, we employed a wild-type and SV40-transformed variant of MRC-5 human fetal lung fibroblasts. Forty-eight hours after treatment with Siomycin A, while the SV40-transformed cells underwent dose dependent apoptosis, the untransformed normal cells did not exhibit significant cell death (FIG. 4C, 4D). This is further supported by our observation that transformed but not normal cells showed cleavage of caspase-3 upon Siomycin A treatment (FIG. 4E). We also investigated the effect of Siomycin A on survivin levels in these cells. Consistent to our previous report (24), we found elevated levels of survivin in the untreated transformed cells relative to normal MRC-5 fibroblasts. Since survivin is a downstream target of FoxM1 (2), Siomycin A was able to effectively repress survivin levels after treatment in both normal and transformed cells (FIG. 4E). Though survivin is downregulated in both cell types, it is interesting to note that apoptosis selectively occurs in the transformed cells. It is possible that in line with the Oncogene addiction hypothesis (25), the transformed cells are more dependent on survivin, depletion of which leads to a more drastic outcome than in the normal cells.

Example 5

Thiostrepton Inhibits FoxM1 Activity

As presented herein, Siomycin A represents a novel inhibitor for oncogenic transcription factor FoxM1. Furthermore, thiostrepton, which has recently been approved for veterinary uses, possesses a similar structure as Siomycin A. Thiostrepton can be prepared and synthesized in laboratory settings. See, for example, reference 29 (J. Am. Chem. Soc. 2005, 127:15042-15044) and reference 30 (U.S. Pat. No. 4,064, 013). Furthermore, fragments of thiostrepton have been shown to exhibit anti-tumor and/or antibacterial activity. See reference 29 (J. Am. Chem. Soc. 2005, 127:15042-15044).

Figure 6:
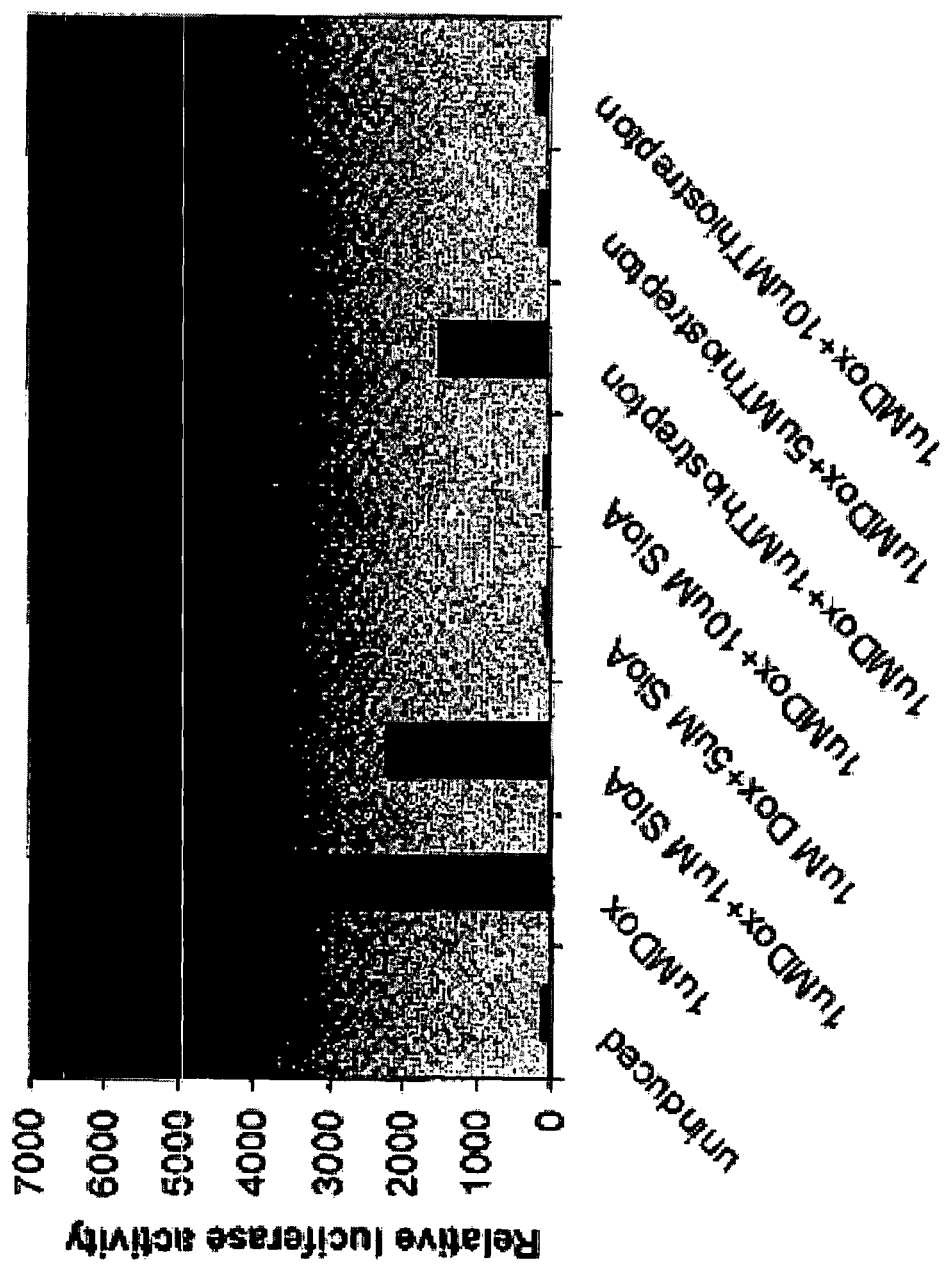
FIG. 6. Thiostrepton and Siomycin A both inhibit FoxM1 transcriptional activity. The C3-Luc cell line derived from U2OS cells was grown in 96-well plates and treated for 24 hrs with the combination of 1 μg/mL doxycyclin and the indicated concentrations of Siomycin A or thiostrepton, respectively. The next day, the luciferase activity was measured with the Dual-Luciferase reporter assay system (E1910; Promega) according to the manufacturer's instructions.

We decided to test if thiostrepton also inhibits FoxM1 transcriptional activity. We used U2OS cell line C3-Luc (described in ref. 31) that stably expresses doxycycline/tetracycline-inducible FoxM1-GFP, firefly luciferase under the control of multiple FoxM1 response elements, and a renilla luciferase under the control of a CMV promoter. We first verified that when doxycycline is added to the medium, FoxM1-GFP is highly induced leading to 60-fold induction in firefly luciferase activity with minimal change in the renilla luciferase activity (FIG. 6). We then used this C3-Luc cell line to test thiostrepton and Siomycin A as a positive control. We found that while the relative firefly luciferase activity was enhanced 60-fold upon induction with doxycycline, addition of 5 µM of thiostrepton and Siomycin A (NSC-285116) efficiently reduced the value to basal levels (FIG. 6). These data suggest that both Siomycin A and thiostrepton are very efficient FoxM1 inhibitors.

Figure 7:
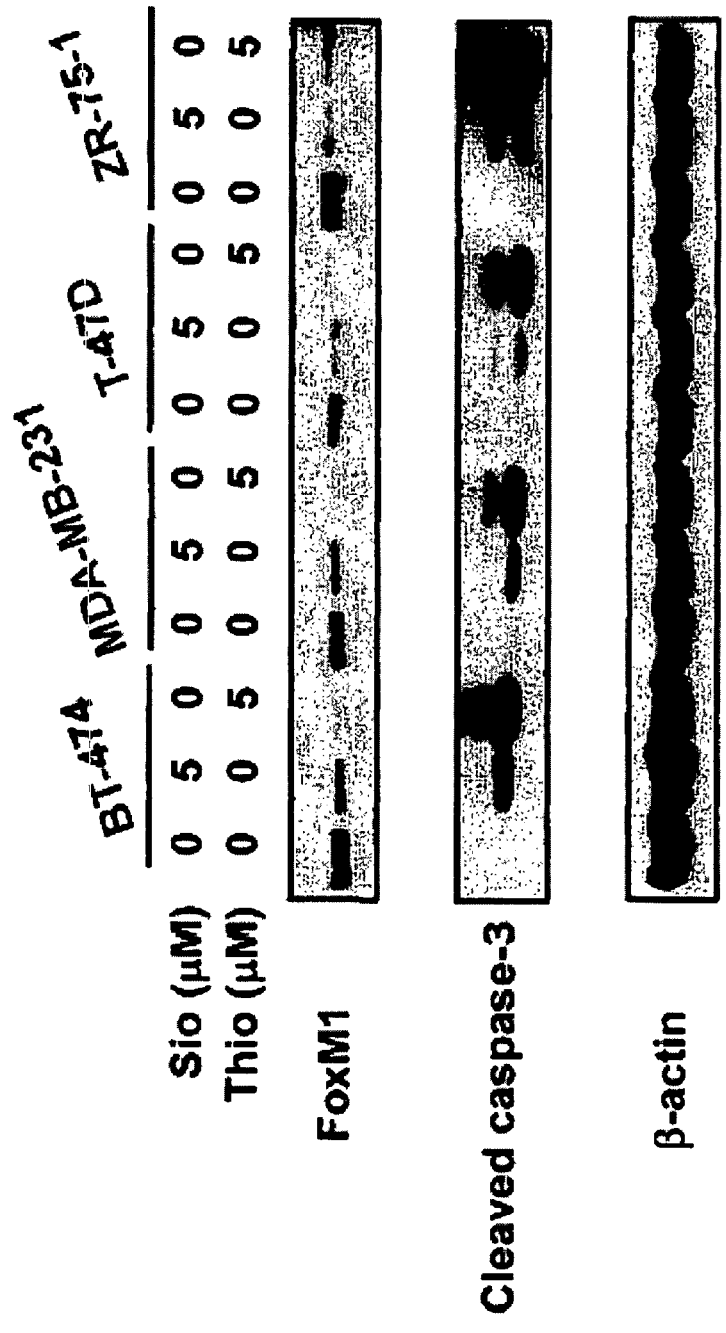
FIG. 7. Siomycin A and thiostrepton inhibit FoxM1 expression and induce apoptosis in breast cancer cell lines. Breast cancer cell lines BT-474, MDA-MB-231, T-47D and ZR-75-1 were treated with 5 μM Siomycin and thiostrepton, respectively, for 48 hrs and the cell lysates were analyzed for the levels of FoxM1 and cleaved caspase-3 by immunoblotting.

To compare the activities of Siomycin A and thiostrepton against FoxM1 and to evaluate their proapoptotic potential in cancer cells we decided to use the panel of human breast cancer cells (FIG. 7). This is a proof of principle experiment because it has been shown that FoxM1 is overexpressed in many breast cancer cells (FIG. 7 and ref. 32). We found correlation between suppression of FoxM1 and induction of apoptosis by these compounds. Furthermore, we found that thiostrepton is a stronger inhibitor of FoxM1 and more efficient inducer of apoptosis than Siomycin A. These data may suggest that Siomycin A and thiostrepton exert their anticancer activity via suppression of FoxM1. However, additional experiments are needed to prove this notion.

In summary, we identified thiostrepton as a compound with similar anticancer properties as Siomycin A. However, thiostrepton is already approved by FDA for animal use as antibacterial drug.

Example 6

FoxM1 is a Positive Effecter of Its Own Transcription

Figure 8:
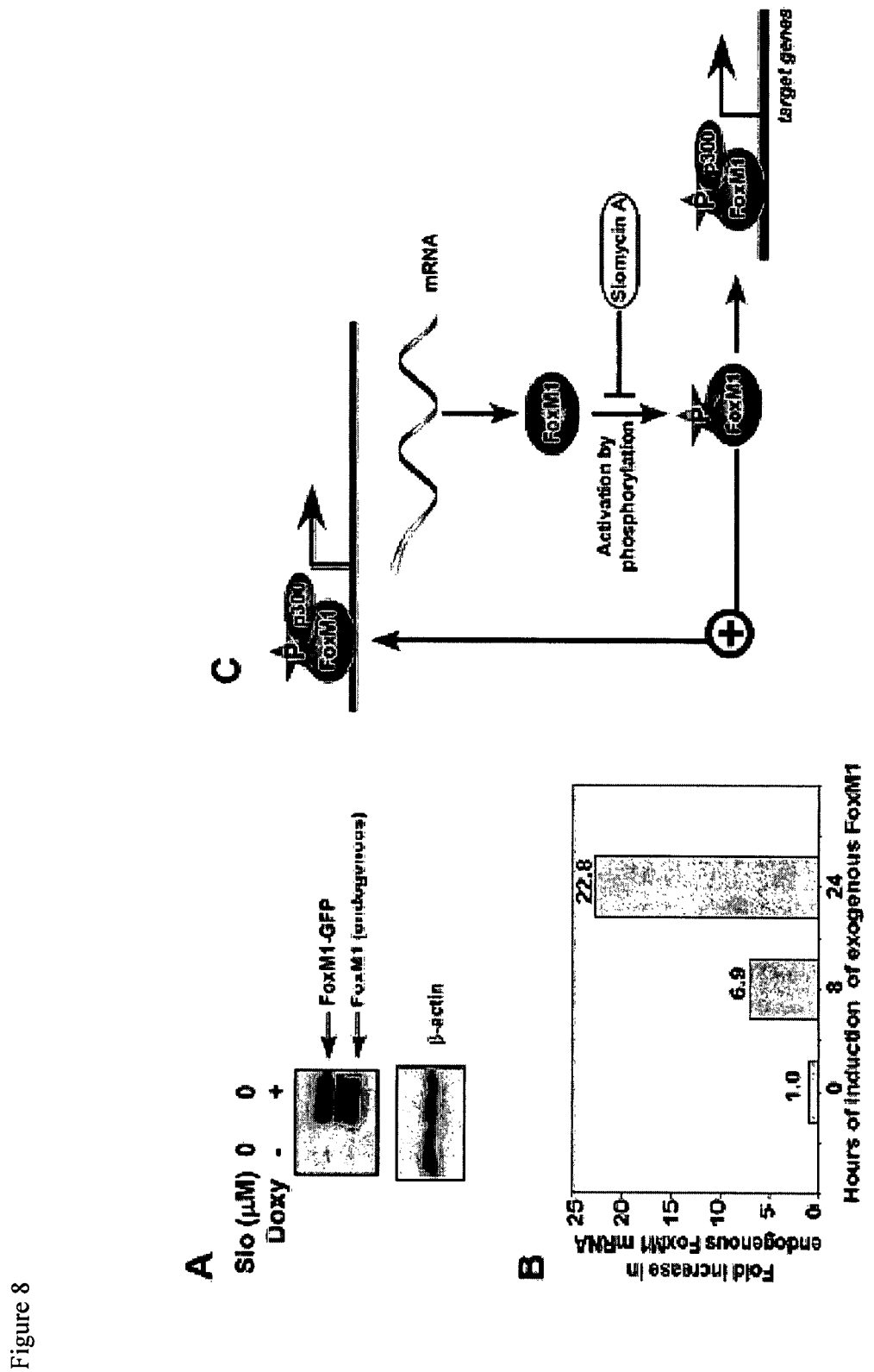
FIG. 8. FoxM1 positive feedback loop and the action of Siomycin A. (A) Exogenous FoxM1 induces expression of endogenous FoxM1 protein. C3-Luc cells with doxycycline-inducible FoxM1-GFP were treated with 1 μg/mL of doxycycline for 24 hours and the cell lysates were used for immunoblotting. (B) Exogenous FoxM1 induces the transcription of endogenous FoxM1 mRNA. C3-Luc cells with doxycycline-inducible FoxM1-GFP were treated with 1 μg/mL of doxycycline for different times and the total RNA was prepared. (C) The model shows that FoxM1 as a transcription factor may bind to its own promoter and induce its own transcription. Siomycin A may inhibit its phosphorylation or may inhibit DNA-binding of FoxM1 to its own promoter.

Siomycin A and thiostrepton inhibit FoxM1/NF-kB dependent transcription and induce apoptosis in human cancer cell lines of different origin During the screening for FoxM1 inhibitors we observed that induction of exogenous FoxM1 led to very strong induction of endogenous FoxM1 protein (FIG. 8A). In order to test the hypothesis that FoxM1 induces its own transcription, we performed real-time quantitative RT-PCR (RT-qPCR) (FIG. 8B). The cell line C3-Luc with doxycycline-inducible FoxM1-GFP (FIG. 1A) was used for these experiments. The exogenous FoxM1-GFP was induced by the addition of doxycycline in the medium and the levels of endogenous FoxM1 mRNA was assessed using primers that are specific for 3'-UTR (primer-S, 5'-TGC CCA GCA GTC TCT TAC CT-3' (SEQ ID NO: 11); and primer-AS, 5'-ACC TTC TGG CAG TCT CTG GA-3' (SEQ ID NO: 12). Levels of cyclophilin (primer-S, 5'-GCA GAC AAG GTC CCA AAG ACA G-3' (SEQ ID NO: 9); and primer-AS, 5'-CAC CCT GAC ACA TAA ACC CTG G-3' (SEQ ID NO: 10)) were used as a control (FIG. 8B). We found that indeed induction of exogenous FoxM1 by doxycycline led to more than a 20-fold up regulation of endogenous FoxM1 mRNA (FIG. 1A) suggesting that FoxM1 is involved in a positive regulatory loop (FIG. 8C). These data suggest that FoxM1 induces its own transcription (FIG. 1B) and therefore inhibition of the transcriptional activity of FoxM1 by Siomycin A will lead to the inhibition of its expression (FIG. 8C).

Example 7

Thiazole Antibiotics Inhibit FoxM1 Expression and Induce Apoptosis in Cancer Cell Lines To test the hypothesis that Siomycin A inhibits not only transcriptional activity, but also the expression of FoxM1 we treated human cancer cell lines with Siomycin A and thiostrepton and we found that this treatment significantly decreased FoxM1 protein levels (FIG. 19-11) in agreement with our assumption. These experiments confirmed that FoxM1 induces its own transcription and when Siomycin A and thiostrepton antagonize the transactivation ability of FoxM1 they also inhibit its expression.

Figure 9:
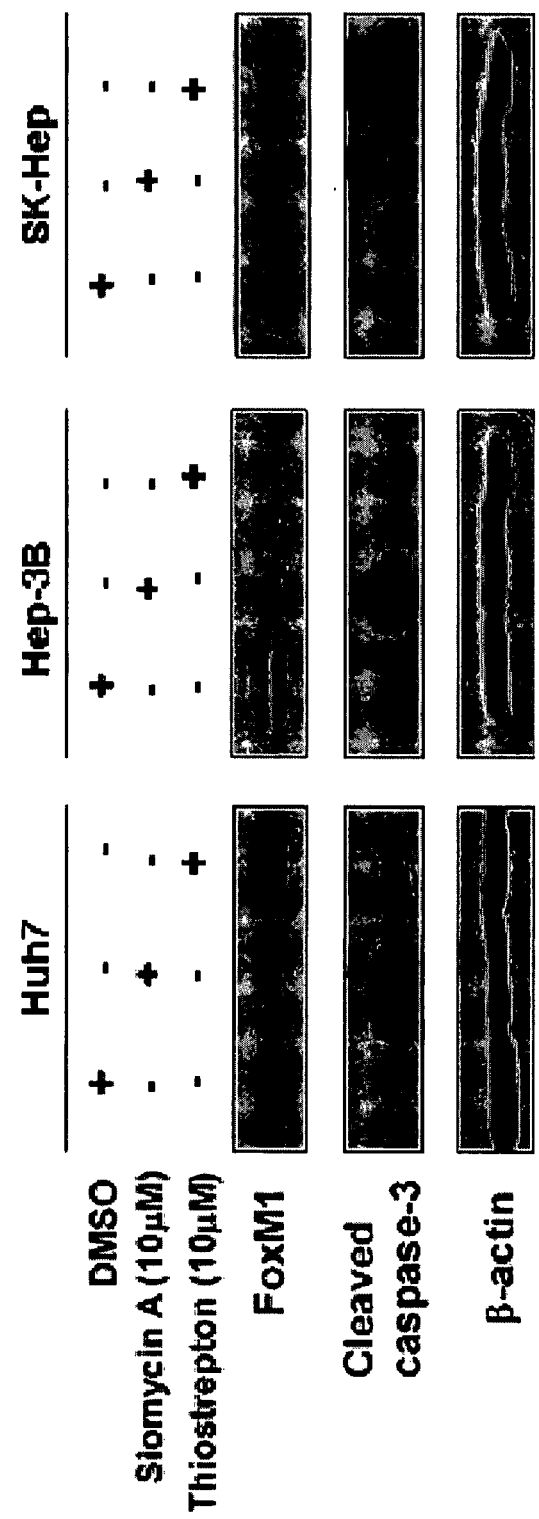
FIG. 9. Siomycin A and thiostrepton inhibit FoxM1 expression and induce apoptosis in liver cancer cell lines. Liver cancer cell lines Huh7, Hep-3B and SK-Hep were treated with 10 μM Siomycin A and thiostrepton, respectively, for 48 hrs, and the cell lysates were analyzed for the levels of FoxM1 and cleaved caspase-3 by immunoblotting.

First, we treated liver cancer cell lines Huh7, Hep-3B and SK-Hep that have deleted or mutant p53 with these compounds for 48 hrs, and the cell lysates were analyzed for the levels of FoxM1 and cleaved caspase-3 by immunoblotting. We found that Siomycin A and thiostrepton both repress FoxM1 protein expression and induce apoptosis in these liver cancer cells (FIG. 9).

Figure 10:
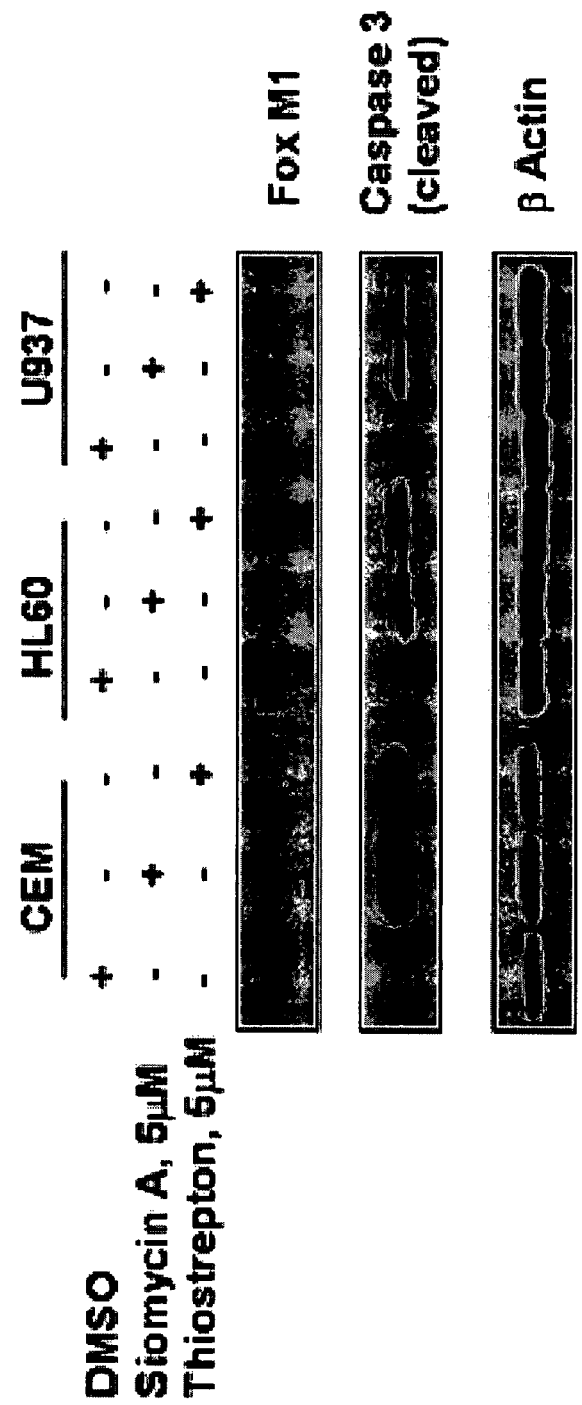
FIG. 10. Siomycin A and thiostrepton inhibit FoxM1 expression and induce apoptosis in leukemia cell lines. Leukemia cell lines CEM, HL60 and U937 were treated with 5 μM Siomycin A and thiostrepton, respectively, for 48 hrs and the cell lysates were analyzed for the levels of FoxM1 and cleaved caspase-3 by immunoblotting.

Next we treated leukemia cell lines with mutant p53 CEM, HL60 and U937 with 5 µM of these compounds for 48 hrs and the cell lysates were analyzed for the levels of FoxM1 and cleaved caspase-3 by immunoblotting. We found that thiazole antibiotics both repress FoxM1 protein expression, and induce apoptosis in these leukemia cells (FIG. 10).

Figure 11:
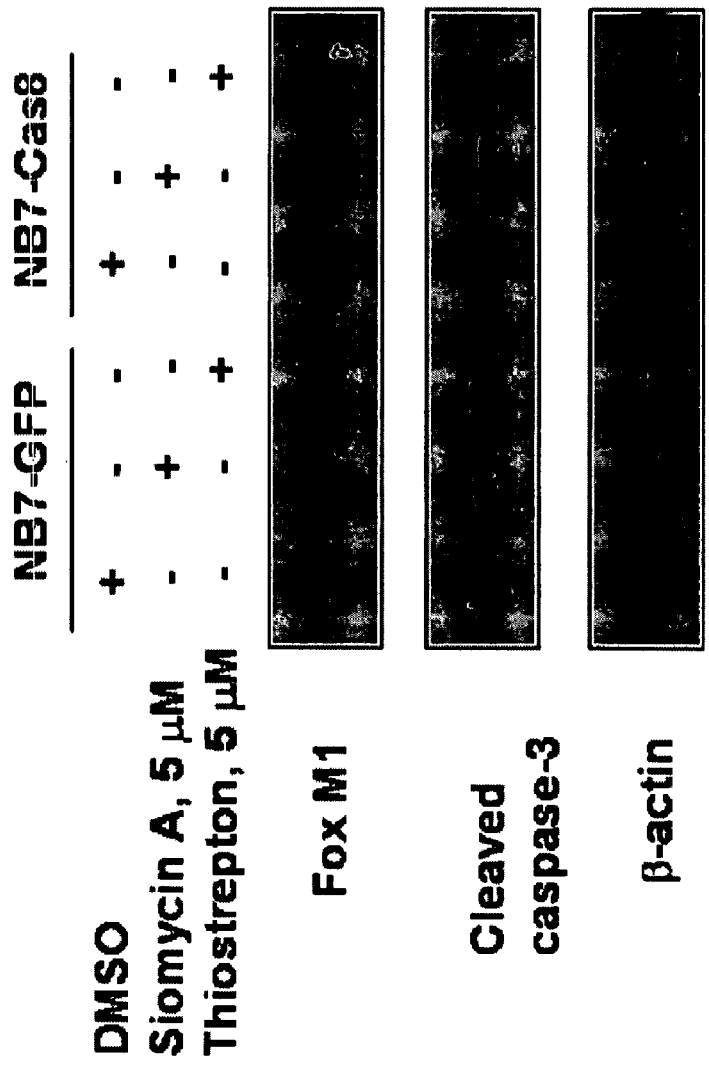
FIG. 11. The thiazoles inhibit expression of FoxM1 and induce apoptosis in neuroblastoma cells. Cells were treated with Siomycin A, thiostrepton or DMSO, harvested 24 hrs later and the lysates were used to determine proteins levels by immunoblotting with antibodies specific for FoxM1, cleaved caspase-3 and β-actin (AS441, Sigma).

To further examine how the thiazole antibiotics induce apoptosis in neuroblastoma cells we treated NB7 and NB7-casp8 (the same cell line with reconstituted caspase-8) cell lines for 24 hrs and the cell lysates were analyzed for the levels of FoxM1 and cleaved caspase-3 by immunoblotting. We found that Siomycin A and thiostrepton both inhibit FoxM1 protein expression and induce apoptosis in these neuroblastoma cells independently from caspase-8 (FIG. 11). These data suggest that the thiazole antibiotics induce apoptosis by intrinsic pathway.

These data show that thiazole antibiotics both antagonize transactivation ability of FoxM1 and also inhibit its expression, because FoxM1 induces its own transcription. In addition, we observed direct correlation between the suppression of FoxM1 and caspase-3 cleavage (induction of apoptosis) by these compounds. The data indicate that Siomycin A and thiostrepton induce p53-independent intrinsic apoptosis in multiple human cancer cell types and exert their activity via the suppression of FoxM1.

Example 8

Thiazole Antibiotics Inhibit Growth of Human Cancer Cells

To evaluate the effect of thiazole antibiotics on growth of human cancer cells we performed a growth inhibition assay on breast cancer cell lines MDA-MB-231, BT 474, T47D; liver cancer cells Hep-3B, Huh 7, SK-Hep; and leukemia cells CEM, HL60 and U937. All cell lines were treated with different doses of thiazole antibiotics for 48 hrs and the growth inhibition was assessed by counting of live cells. These cell lines displayed IC50 from 0.5 to 5.0 µM, suggesting that 50% cell growth inhibition by the thiazole antibiotics was achieved in low micromolar concentrations and that human cancer cells of different origin are sensitive to growth inhibition and cell death induced by thiazole antibiotics. Results are depicted in FIG. 12.

Example 9

Figure 13:
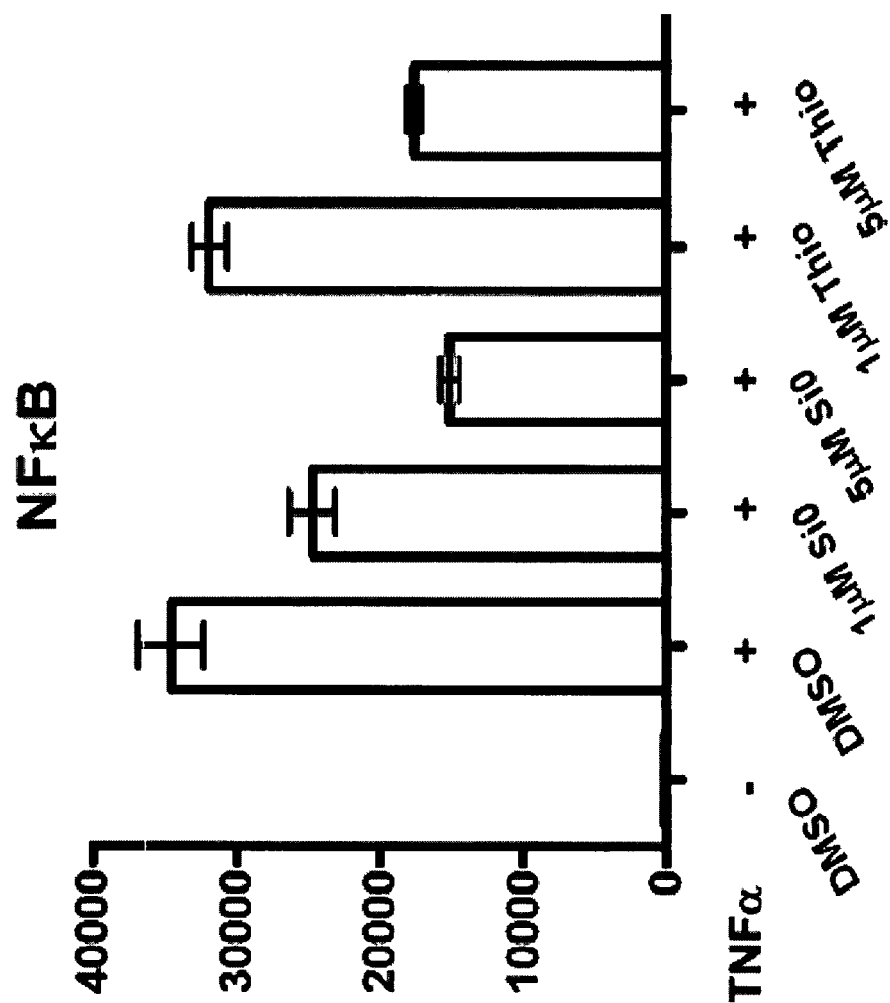
FIG. 13. Siomycin A and thiostrepton both inhibit NF-kB transcriptional activity. 293T cells stably expressing an NF-kB-Luc reporter construct were grown in 6-well plates and treated with 10 ng/ml TNF-alpha. Twenty-four hours later the cells were treated with the indicated concentrations of Siomycin A and thiostrepton for 10 hours, and the luciferase activity was measured using the Dual-Luciferase Reporter Assay System (Promega) according to the manufacturer's recommendations.
Figure 14:
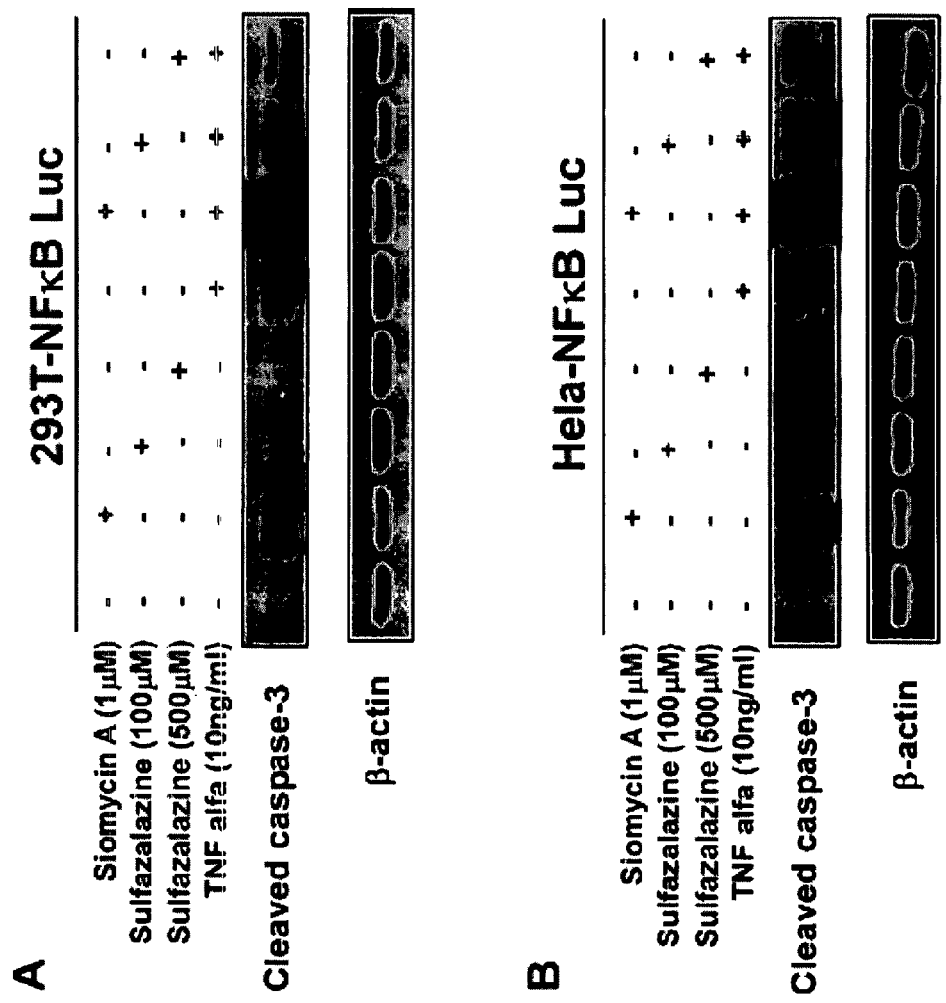
FIG. 14. Siomycin A sensitize human cancer cells to TNF-alpha-induced apoptosis. 293 (A) and Hela (B) cells were pretreated with the indicated concentrations of Sulfazalazine (control) for overnight. The following day the cells were treated with 1 μM Siomycin A and 10 ng/ml TNF-alpha as indicated. Twenty-four hours later the cells were harvested and the total cell lysates were used to determine the level of cleaved caspase-3. β-actin was used as the loading control.

Thiazole Antibiotics Inhibit NF-kB Dependent Transcription and Sensitize Human Cancer Cells to TNF-alpha Induced Apoptosis Next we evaluated how thiazole antibiotics may affect other transcription factors, such as p53, Tcf/Lef, Gli1, or NF-kB. We found that thiazole antibiotics do not affect p53, Tcf/Lef, Gli1 (data not shown), but they repress NF-kB-dependent transcription (FIG. 13). In addition, we found that Siomycin A sensitize human cancer cells to TNF-alpha-induced apoptosis (FIG. 14). These data suggest that thiazole antibiotics are bitargeted anticancer drugs that may simultaneously inhibit two pro-cancer pathways: FoxM1 and NF-kB.

It is understood that the disclosed invention is not limited to the particular methodology, protocols, and reagents described as these may vary.

Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

REFERENCES

Each of the following references is incorporated herein by reference in its entirety, particularly in parts pertinent to the subject matter for which it is cited herein above.

1. Laoukili J, Kooistra M R, Bras A, et al. FoxM1 is required for execution of the mitotic programme and chromosome stability. Nat Cell Biol 2005; 7:126-36.
2. Wang I C, Chen Y J, Hughes D, et al. Forkhead box M1 regulates the transcriptional network of genes essential for mitotic progression and genes encoding the SCF (Skp2-Cks1) ubiquitin ligase. Mol Cell Biol 2005; 25:10875-94.
3. Costa R H. FoxM1 dances with mitosis. Nat Cell Biol 2005; 7:108-10.
4. Ye H, Kelly T F, Samadani U, et al. Hepatocyte nuclear factor 3/fork head homolog 11 is expressed in proliferating epithelial and mesenchymal cells of embryonic and adult tissues. Mol Cell Biol 1997; 17:1626-41.
5. Ye H, Holterman A X, Yoo K W, Franks R R, Costa R H. Premature expression of the winged helix transcription factor HFH-11B in regenerating mouse liver accelerates hepatocyte entry into S phase. Mol Cell Biol 1999; 19:8570-80.
6. Korver W, Roose J, Clevers H. The winged-helix transcription factor Trident is expressed in cycling cells. Nucleic Acids Res 1997; 25:1715-9.
7. Yao K M, Sha M, Lu Z, Wong G G. Molecular analysis of a novel winged helix protein, WIN. Expression pattern, DNA binding property, and alternative splicing within the DNA binding domain. J Biol Chem 1997; 272:19827-36.
8. Wonsey D R, Follettie M T. Loss of the forkhead transcription factor FoxM1 causes centrosome amplification and mitotic catastrophe. Cancer Res 2005; 65:5181-9.
9. Teh M T, Wong S T, Neill G W, Ghali L R, Philpott M P, Quinn A G. FOXM1 is a downstream target of Gli1 in basal cell carcinomas. Cancer Res 2002; 62:4773-80.
10. Okabe H, Satoh S, Kato T, et al. Genome-wide analysis of gene expression in human hepatocellular carcinomas using cDNA microarray: identification of genes involved in viral carcinogenesis and tumor progression. Cancer Res 2001; 61:2129-37.
11. Lee J S, Chu I S, Heo J, et al. Classification and prediction of survival in hepatocellular carcinoma by gene expression profiling. Hepatology 2004; 40:667-76.
12. Obama K, Ura K, Li M, et al. Genome-wide analysis of gene expression in human intrahepatic cholangiocarcinoma. Hepatology 2005; 41:1339-48.
13. Kim I M, Ackerson T, Ramakrishna S, et al. The Forkhead Box m1 transcription factor stimulates the proliferation of tumor cells during development of lung cancer. Cancer Res 2006; 66:2153-61.
14. van den Boom J, Wolter M, Kuick R, et al. Characterization of gene expression profiles associated with glioma progression using oligonucleotide-based microarray analysis and real-time reverse transcription-polymerase chain reaction. Am J Pathol 2003; 163:1033-43.
15. Kalin T V, Wang I C, Ackerson T J, et al. Increased levels of the FoxM1 transcription factor accelerate development and progression of prostate carcinomas in both TRAMP and LADY transgenic mice. Cancer Res 2006; 66:1712-20.

16. Pilarsky C, Wenzig M, Specht T, Saeger H D, Grutzmann R. Identification and validation of commonly overexpressed genes in solid tumors by comparison of microarray data. Neoplasia 2004; 6:744-50.
17. Kalinichenko V V, Major M L, Wang X, et al. Foxm1b transcription factor is essential for development of hepatocellular carcinomas and is negatively regulated by the p19RF tumor suppressor. Genes Dev 2004; 18:830-50.
18. Radhakrishnan S K, Feliciano C S, Najmabadi F, et al. Constitutive expression of E2F-1 leads to p21-dependent cell cycle arrest in S phase of the cell cycle. Oncogene 2004; 23:4173-6.
19. Radhakrishnan S K, Gartel A L. The PPAR-gamma agonist pioglitazone post-transcriptionally induces p21 in PC3 prostate cancer but not in other cell lines. Cell Cycle 2005; 4:582-4.
20. Radhakrishnan S K, Gierut J, Gartel A L. Multiple alternate p21 transcripts are regulated by p53 in human cells. Oncogene 2006; 25:1812-5.
21. Conzen S D, Gottlob K, Kandel E S, et al. Induction of cell cycle progression and acceleration of apoptosis are two separable functions of c-Myc: transrepression correlates with acceleration of apoptosis. Mol Cell Biol 2000; 20:6008-18.
22. Major M L, Lepe R, Costa R H. Forkhead box M1B transcriptional activity requires binding of Cdk-cyclin complexes for phosphorylation-dependent recruitment of p300/CBP coactivators. Mol Cell Biol 2004; 24:2649-61.
23. Lentzen G, Klinck R, Matassova N, Aboul-ela F, Murchie A I. Structural basis for contrasting activities of ribosome binding thiazole antibiotics. Chem Biol 2003; 10:769-78.
24. Radhakrishnan S K, Gartel A L. A novel transcriptional inhibitor induces apoptosis in tumor cells and exhibits antiangiogenic activity. Cancer Res 2006; 66:3264-70.
25. Weinstein I B. Cancer. Addiction to oncogenes—the Achilles heal of cancer. Science 2002; 297:63-4.
26. Hagg M, Biven K, Ueno T, et al. A novel high-through-put assay for screening of pro-apoptotic drugs. Invest New Drugs 2002; 20:253-9.
27. Erdal H, Berndtsson M, Castro J, Brunk U, Shoshan M C, Linder S. Induction of lysosomal membrane permeabilization by compounds that activate p53-independent apoptosis. Proc Natl Acad Sci USA 2005; 102:192-7.
28. Monga M, Sausville E A. Developmental therapeutics program at the NCI: molecular target and drug discovery process. Leukemia 2002; 16:520-6.
29. Nicolaou K C, Zak M, Rahimipour S, Estrada A, Lee S H, O'Brate A, Giannakakou P, Ghadiri M R. Discovery of a Biologically Active Thiostrepton Fragment. J. Am. Chem. Soc. 2005; 127:15042-15044.
30. U.S. Pat. No. 4,064,013. Process For Preparing Thiostrepton.
31. Radhakrishnan, S. K., Bhat, U. G., Hughes, D. E., Wang, I. C., Costa, R. H., and Gartel, A. L. Identification of a Chemical Inhibitor of the Oncogenic Transcription Factor Forkhead Box M1. Cancer Res, 66: 9731-9735, 2006.
32. Madureira, P. A., Varshochi, R., Constantinidou, D., Francis, R. E., Coombes, R. C., Yao, K. M., and Lam, E. W. The Forkhead box M1 protein regulates the transcription of the estrogen receptor alpha in breast cancer cells. J Biol Chem, 281: 25167-25176, 2006.
33. Smith, C. A., Farrah, T., and Goodwin, R. G. Cell, 76: 959-962, 1994.
34. Ashkenazi, A., and Dixit, V. M. Curr. Opin. Cell Biol., 11: 255-260, 1999.
35. Ashkenazi, A., and Dixit, V. M. Science, 281: 1305-1308, 1998.
36. Schulze-Osthoff, K., Ferrari, D. Los, M., Wesselborg, S., and Peter, M. Eur. J. Biochem, 254: 439-459, 1998.
37. Van Antwerp, D. J., Martin, S. J., Verma, I. M., and Green, D. R. Trends Cell Bio., 8: 107-111, 1998.
38. Nagata, S., and Golstein, P. Science, 267: 1449-1456, 1995.
39. Griffith, T. S., and Lynch, D. H. Curr. Opin. Immunol, 10: 559-563, 1996.
40. Yeh, W. C., Pompa, J. L., McCurrach, M. E., Shu, H. B., Elia, A. J., Shahinian, A., Ng, M., Wakeham, A., Khoo, W., Mitchell, K., El-Deiry, W. S., Lowe, S. W., Goeddel, D. V., and Mak, T. W. Science, 279: 1954-1958, 1998.
41. Muzio, M., Chinnaiyan, A. M., Kischkel, F. C., O'Rourke, K., Shevchenko, A., Ni, J., Scaffidi, C., Bretz, J. D., Zhang, M. Gentz, R., Mann, M., Krammer, P. H., Peter, M. E., and Dixit, V. M. Cell 85: 817-827, 1996.
42. Hsu, H., Shu, H. B., Pan, M. G., and Goeddel, D. V. Cell 84: 299-308, 1996.
43. Boldin, M. P., Goncharov, T. M., Goltsev, Y. V., and Walsh, D. Cell, 85: 803-15, 1996.

What is claimed is:

1. A method for identifying a compound that inhibits FoxM1 transcriptional activity in vitro, comprising:
   (A) providing a cell comprising (i) a FoxM1 gene that encodes a polypeptide having the amino acid sequence as identified by SEQ ID NO: 14 operably linked to a first transcription control unit responsive to an effector, (ii) a second gene encoding a first reporter protein operably linked to a second transcriptional control unit responsive to FoxM1; and (iii) a third gene encoding a second reporter protein operably linked to a third transcription control unit for constitutive transcription thereof, wherein said first and second reporter proteins engender first and second detectable signals that are distinguishable from each other,
   (B) exposing said cell to said effector and optionally to the compound and measuring said first and second signals in the absence and in the presence of said compound, wherein the cell is exposed to a level of said effector that maximizes the signal engendered by said first reporter protein, and
   (C) identifying a compound that inhibits FoxM1 transcriptional activity when the levels of the first signal are decreased in the presence of the compound relative to the levels of the first signal in the absence of the compound, and wherein the levels of the second signal are substantially the same in the presence and absence of the compound.

2. The method of claim 1, wherein the first reporter protein is firefly luciferase.

3. The method of claim 2, wherein the second reporter protein is renilla luciferase.

4. The method of claim 1, wherein the effector is doxycycline or tetracycline.

5. The method of claim 1, wherein the method is adapted for high-throughput screening of compounds.

6. The method of claim 1, wherein the FoxM1 gene is an exogenous FoxM1 gene.

7. A method for high throughput screening of a plurality of compounds for identifying a compound that inhibits FoxM1 activity in vitro, comprising:
   (A) providing a plurality of cells comprising (i) a FoxM1 gene that encodes a polypeptide having the amino acid sequence as identified by SEQ ID NO: 14 operably linked to a first transcription control unit responsive to an effector, (ii) a second gene encoding a first reporter protein operably linked to a second transcriptional control unit responsive to FoxM1; and (iii) a third gene encoding a second reporter protein operably linked to a third transcription control unit for constitutive transcription thereof, wherein said first and second reporter proteins engender first and second detectable signals that are distinguishable from each other, and wherein the method is adapted for high-throughput screening of compounds,
   (B) exposing said plurality of cells to said effector and optionally to a plurality of compounds and measuring said first and second signals in the absence and in the presence of said plurality of compounds, and
   (C) identifying a compound that inhibits FoxM1 transcriptional activity when the levels of the first signal are decreased in the presence of the compound relative to the levels of the first signal in the absence of the compound, and wherein the levels of the second signal are substantially the same in the presence and absence of the compound.

8. The method of claim 7, wherein the first reporter protein is firefly luciferase.

9. The method of claim 7, wherein the second reporter protein is renilla luciferase.

10. The method of claim 7, wherein the cell is exposed to a level of said effector that maximizes the signal engendered by said first reporter protein.

11. The method of claim 7, wherein the FoxM1 gene is an exogenous FoxM1 gene.

* * * * *